(12) United States Patent
Bailey et al.

(10) Patent No.: US 8,734,457 B2
(45) Date of Patent: May 27, 2014

(54) INSTRUMENT FOR USE IN A JOINT REPLACEMENT PROCEDURE

(75) Inventors: Andrew Bailey, Leeds (GB); Steven Gowers, Leeds (GB)

(73) Assignee: Depuy International Limited (GB)

( * ) Notice: Subject to any disclaimer, the term of this patent is extended or adjusted under 35 U.S.C. 154(b) by 625 days.

(21) Appl. No.: 12/919,140

(22) PCT Filed: Feb. 5, 2009

(86) PCT No.: PCT/GB2009/050112
§ 371 (c)(1),
(2), (4) Date: Nov. 23, 2010

(87) PCT Pub. No.: WO2009/106867
PCT Pub. Date: Sep. 3, 2009

(65) Prior Publication Data
US 2011/0060418 A1 Mar. 10, 2011

(30) Foreign Application Priority Data
Feb. 29, 2008 (GB) .................................. 0803723.6

(51) Int. Cl.
*A61B 17/58* (2006.01)
*A61B 17/60* (2006.01)
*A61F 2/00* (2006.01)

(52) U.S. Cl.
USPC ....... 606/91; 623/22.11; 623/22.12; 606/86 R

(58) Field of Classification Search
USPC ............ 623/22.11, 22.12, 22.4–22.42, 23.39, 623/23.11; 606/91, 99, 86 R, 100
See application file for complete search history.

(56) References Cited

U.S. PATENT DOCUMENTS

| | | | |
|---|---|---|---|
| 6,206,925 B1 | 3/2001 | Tornier | |
| 6,228,120 B1 | 5/2001 | Leonard | |
| 6,719,799 B1 | 4/2004 | Kropf | |
| 6,736,852 B2 * | 5/2004 | Callaway et al. | 623/19.14 |
| 2001/0053935 A1 * | 12/2001 | Hartdegen et al. | 623/19.12 |
| 2002/0120339 A1 | 8/2002 | Callaway | |
| 2005/0033443 A1 | 2/2005 | Blatter | |
| 2005/0197708 A1 * | 9/2005 | Stone et al. | 623/19.12 |

FOREIGN PATENT DOCUMENTS

| | | |
|---|---|---|
| DE | 19841612 A1 | 3/2000 |
| EP | 807426 A2 | 11/1997 |
| WO | WO 2004030581 A2 | 4/2004 |
| WO | WO 2004030581 A3 | 7/2004 |
| WO | WO 2005086939 A2 | 9/2005 |
| WO | WO 2006136954 A1 | 12/2006 |

OTHER PUBLICATIONS

GB Search Report GB0803723.6, dated May 30, 2008.
International Search Report and Written Opinion PCT/GB2009/050112, dated May 28, 2009.

* cited by examiner

*Primary Examiner* — Matthew Lawson
*Assistant Examiner* — Si Ming Lee

(57) ABSTRACT

An instrument for use in a joint replacement procedure includes a trial head that corresponds to the head of an orthopaedic joint component having an upper surface defined by a curved surface and a bore formed in a lower surface and a trial connector for connecting the trial head to a stem part of the orthopaedic joint component which is intended for location in the intramedullary cavity of a bone. The trial connector can be fitted into the bore in the trial head at a variable angular orientation.

18 Claims, 14 Drawing Sheets

INSTRUMENT FOR USE IN A JOINT REPLACEMENT PROCEDURE

CROSS REFERENCE TO RELATED PCT APPLICATION

This application is a National Stage 35 U.S.C. 371 of International Patent Application PCT/GB2009/050112 filed Feb. 5, 2009.

BACKGROUND OF THE INVENTION

This invention relates to an instrument for use in a joint replacement procedure.

The success of a joint replacement procedure depends in part on the appropriate alignment of the articulating parts of the joint prosthesis. Inappropriate alignment can give rise to post-operative problems, including limited range of motion of the joint, wear of the bearing surfaces which is uneven or excessive, and damage to soft tissue which is associated with the joint.

It is known to construct the humeral component of a shoulder joint prosthesis using a stem part, a head part, and a connector part which can be fitted into a bore in the head part, and has a bore formed in it to receive a spigot on the stem part. Such a device is disclosed in US-A-2005/0197708. The eccentric arrangement of the bore in the head part relative to the axis of the head part, and the eccentric arrangement of the bore in the connector part eccentric relative to the axis of the connector part, allow the distance through which the head part is offset relative to the stem part, and the orientation of that offset, to be adjusted to suit the requirements of a patient. This can facilitate variation of effective arm length, and the extent of retroversion and anteversion.

It is known to use trial implant instruments in a surgical procedure to implant an orthopaedic prosthesis. The use of a trial instrument has the advantage that the configuration of the instrument can be assessed in relation to a mating instrument or implant with a view to selecting the ultimate implant component with the optimum configuration.

US-A-2001/0053935 discloses a trialling system which comprises a plurality of components. It is suitable for use in conjunction with an implant which also comprises a plurality of modular components. The modular trial implant instrument can then enable the configuration of the trial implant instrument to be changed to identify an optimum configuration.

It is known for trialling systems to incorporate markings to allow for easy identification of the configuration of the trial implant instrument such that this information can be recorded and transferred to the final orthopaedic prosthesis. In particular, for trialling systems in which the head part can be offset relative to the stem part, markings can be provided to indicate the orientation of the head part (that is, the direction of maximum eccentricity). However, depending upon the configuration chosen for the trial implant instrument, the markings may not be easily visible to a surgeon. For instance, if a significant degree of anteversion is applied to a trial implant instrument which includes a marker indicating the radial direction of maximum eccentricity (for a predetermined magnitude of the offset), the marker may be obscured within the wound. The problem is particularly acute for minimally invasive surgery where visibility of implants and trial implant instruments in general is limited. Limited visibility can result in misidentification of the correct marking indicating the radial direction of maximum eccentricity.

BRIEF SUMMARY OF THE INVENTION

It is an object of embodiments of the present invention to obviate or mitigate one or more of the problems associated with the prior art, whether identified herein or elsewhere.

According to a first aspect of the present invention there is provided an instrument for use in a joint replacement procedure, which comprises: a trial head which corresponds to the head of an orthopaedic joint component having an upper surface defined by a curved surface and a bore formed in a lower surface; a trial connector for connecting the trial head to a stem part of the orthopaedic joint component which is intended for location in the intramedullary cavity of a bone, in which the trial connector can be fitted into the bore in the trial head at a variable angular orientation; and a rotating indicator pivotally coupled about a polar axis of the trial head which is defined by the curved upper surface, the rotating indicator being arranged to couple to a stem part of the orthopaedic joint component connected to the trial connector such that the rotational position of the rotating indicator about the polar axis is indicative of the rotational position of the trial connector within the bore in the trial head; wherein the bore in the lower surface of the trial head is eccentric of the polar axis and the connection between the trial connector and the stem part of the orthopaedic joint component is eccentric of the centre of the trial connector, and wherein a predetermined point on the rotating indicator is indicative of the direction of maximum eccentricity of the trial head relative to the connection between the trial connector and the stem of the orthopaedic component.

An advantage of the present invention is that the radial direction of maximum eccentricity for the trial head is clearly indicated by the rotating indicator, which advantageously avoids the risk of misidentification of the correct marking on a trial head, which could otherwise result in the direction of maximum eccentricity being misaligned.

Preferably, the rotating indicator includes at least one edge arranged to engage the stem part of the orthopaedic joint component such that the rotational position of the rotating indicator about the polar axis is indicative of the rotational position of the trial connector within the bore in the trial head.

The rotating indicator may comprise a disc coupled to the lower surface of the trial connector about the polar axis, the disc extending at least in part to overlap the connection between the trial connector and the stem part of the orthopaedic joint component. The disc may be a circular disc approximately the same diameter as that of the lower surface of the trial head. The disc may further comprise one of a raised annular portion and a corresponding annular recess extending about the polar axis and the lower surface of the trial head comprises the other of a raised annular portion and a corresponding annular recess, the raised portion being receivable in the recess to pivotally couple the rotating indicator to the lower surface of the trial head about the polar axis.

The rotating indicator may be pivotally coupled to the trial head via at least one portion of the rotating indicator extending from the lower surface of the trial head to overlap the upper surface of the trial head.

The rotating indicator may further comprise at least one arm extending from proximal to the polar axis towards the connection between the trial connector and the stem part of the orthopaedic joint component such that the rotational position of the rotating indicator about the polar axis is indicative of the rotational position of the trial connector within the bore in the trial head.

The rotating indicator may comprise a pair of parallel arms arranged to engage opposite sides of the stem part of the orthopaedic joint component. The pair of parallel arms may comprise the sides of a closed slot.

The trial connector may have a bore formed in a lower surface to receive the stem part of the orthopaedic joint component, the trial connector further comprising a skirt portion extending from the lower surface of the trial head such that the edge of the rotating indicator engages the stem part of the orthopaedic joint component via the skirt portion.

The bore in the trial head may be located eccentrically relative to the polar axis of the trial head, the connector sleeve further comprising an inwardly tapered bore with a circular cross section located eccentrically relative to the axis of the connector sleeve for cooperation with the stem part of the orthopaedic joint component.

The trial connector may comprise a body part and a trigger which can be moved relative to the body part between an unlocked position in which the connector can be moved relative to the head part between different ones of a plurality of angular orientations relative to the trial head and a locked position in which the trial connector is restrained against such movement. The trial connector and the trial head may present a cooperating rib and groove arrangement which, when the rib is engaged in the groove, resists angular adjustment of the trial connector within the bore of the trial head. The rib and groove arrangement may define not more than ten angular positions of the trial connector relative to the trial head. The rotational position of the trial connector in the trial head bore may determine the rotational position of the rotating indicator.

The rotational position of the rotating indicator may determine the rotational position of the trial connector in the trial head bore. Rotating the rotating indicator relative to the trial head may cause the trial connector to rotate within the trial head bore.

According to a second aspect of the present invention there is provided an assembly for use in a joint replacement procedure, which comprises: an instrument as described above; and an orthopaedic joint component which comprises: a head part having the shape of a truncated sphere with a convex bearing surface which can engage and articulate with a socket component and an opposite reverse face, the head part having a blind bore with a circular cross section within it located eccentrically relative to the axis of the head part, in which the bore extends into the head part from an opening on the reverse face and is inwardly tapered continuously from the opening towards the blind end thereof; a stem part having a distal end and a head end, which can be fitted distal end first into a bone cavity; and a connector sleeve part with a circular cross-section which is tapered inwardly along the axis defined by its external surface so that it can be received snugly in the tapered bore in the head part.

The instrument of the invention can be made from materials which are commonly used in the manufacture of surgical instruments. Examples of such materials include metals and polymers. Examples of suitable metals which might be used in the instrument of the invention include certain stainless steels, as well as alloys of elements such as titanium. Examples of polymers which might be used in the instrument of the invention include engineering polymers such as polyaryl ether ketones, polyetherether ketones, certain polyamides and polyesters, polyolefins such as certain polyethylenes and polypropylenes, and so on. The properties of the polymer can be adapted to suit particular requirements by addition of a filler, especially a particulate filler.

It can be appropriate for the instrument of the invention to be used in a hip joint replacement procedure, in which case the instrument can include a stem part which can be fitted into the intramedullary cavity of a patient's femur. The trial head can be arranged to articulate with a cup component which can be placed in the patient's acetabulum. Alternatively, the trial head can articulate against the natural acetabulum if the trial head is being used during a hemi-arthroplasty. Alternatively, the instrument of the invention may be used in a shoulder joint replacement procedure, in which case the instrument can include a stem part which can be fitted into the intramedullary cavity of a patient's humerus. The trial head can be arranged to articulate with the patient's glenoid or with the glenoid component which can be fitted in the patient's glenoid.

BRIEF DESCRIPTION OF THE DRAWINGS

Embodiments of the invention will now be described by way of example with reference to the accompanying drawings, in which.

DETAILED DESCRIPTION OF THE INVENTION

Figures 1, 2:
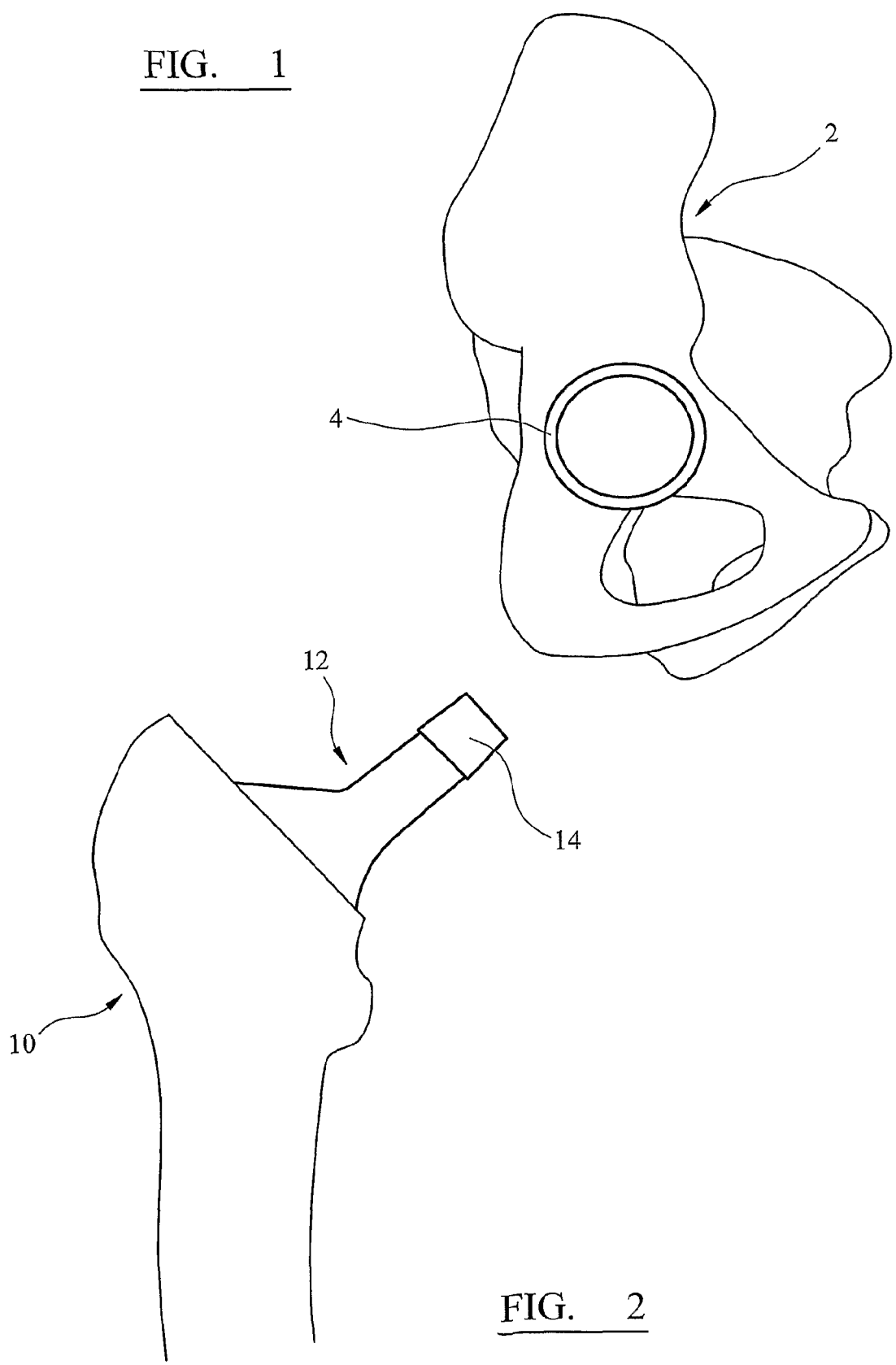
FIG. 1 is a view of a prepared acetabulum, in which an acetabular cup component has been implanted.
FIG. 2 is a view along the anterior posterior axis of the head of a femur, in which a stem part of a femoral component of a hip joint prosthesis has been implanted.

Referring to the drawings, FIG. 1 shows a pelvis 2 which has been reamed to receive the acetabular cup component 4 of a hip joint prosthesis. The acetabular cup component has been implanted using conventional techniques.

FIG. 2 shows the head portion of a femur 10 which has been resected at the base of the femoral neck. The intramedullary cavity has been prepared using conventional techniques (by reaming or broaching or a combination of the two) to receive the stem part 12 of the femoral component of a hip joint prosthesis. The stem part can be fastened in the femur by means of a bone cement material, as is known. The stem part can be fastened in the femur without the use of a bone cement material, as is known.

The stem part has a tapered spigot 14 at its exposed end on which the head part of the femoral component can be fitted. The dimensions of the spigot on the stem part are in line with existing stem parts of femoral components of hip joint prostheses.

Figure 3:
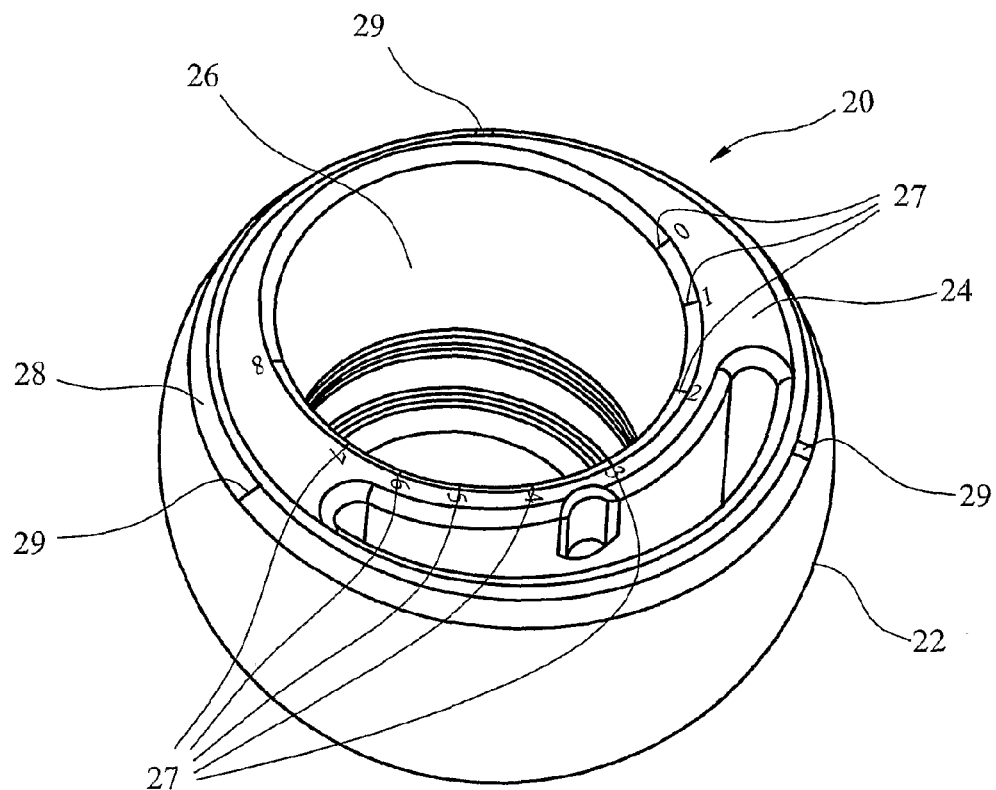
FIG. 3 is a view from below of a head part of a femoral component.

FIG. 3 shows the head part 20 of a femoral component of a hip joint prosthesis according to the present invention. The head part has a spherical bearing surface 22 and an opposite reverse face 24. The spherical bearing surface extends through an angle of arc of about 200°. The radius of the bearing surface is 18 mm. The distance from the reverse face of the head part to the point where the polar axis intersects the bearing surface is from 28.25 to 41.8 mm.

A tapered bore 26 is formed in the reverse face 24. The bore has a circular cross-section. At the reverse face, the diameter of the bore is from 24.2 to 28.6 mm. The depth of the bore, measured from the reverse face of the head part to the blind end of the bore, is from 9.0 to 11.5 mm. The angle between the wall of the bore and its axis (which is half of the angle defined by the diametrically opposite walls of the bore) is 5°.

The bore 26 is offset relative to the polar axis (which is the axis extending through the centre of the sphere defined by the bearing surface, perpendicular to the reverse face). The distance between the axis of the bore and the polar axis is from 2 to 4 mm.

The head part has a series of markings 27 on its reverse face. These relate to the distance through which the head part is offset relative to the axis of the stem part when the femoral component is assembled, as discussed below.

The head component has a chamfer surface 28 extending around its periphery where the bearing and reverse faces come together. The chamfer surface is planar when the component is viewed in cross-section. The angle between the chamfer surface and the polar axis is about 50°. The chamfer surface has three markings 29 at spaced apart points. The markings are distinguishable from one another.

Figure 4:
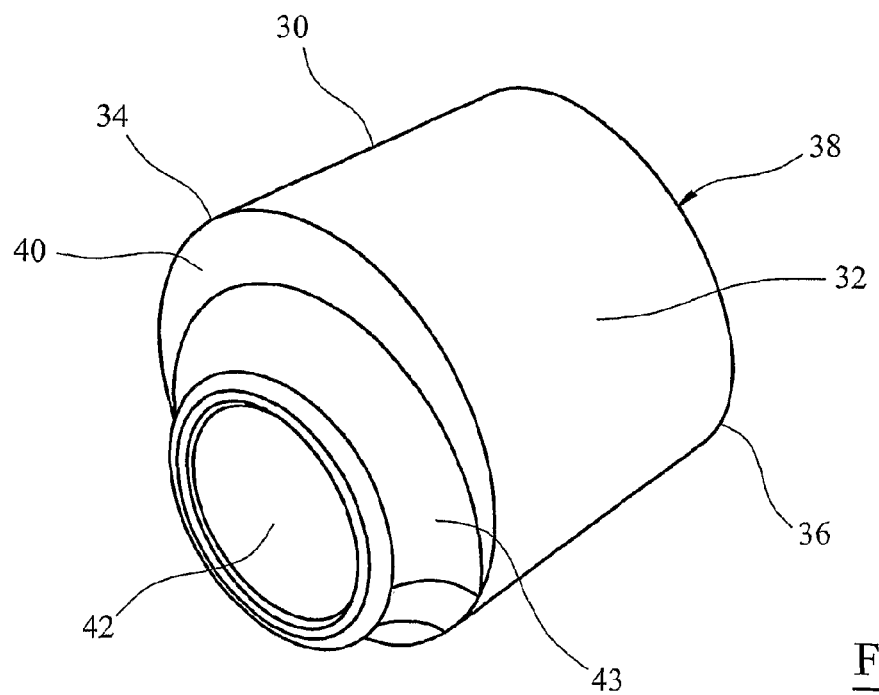
FIG. 4 is an isometric view from below of a connector in place which can be used to connect the head part shown in FIG. 3 to the stem part shown in FIG. 2.

FIG. 4 shows a connector 30 which can be used to connect the head part to the stem part 12 of the femoral component. The connector is circular when viewed from above and is tapered inwardly along the axis defined by its external surface 32. The diameter of the connector at its widest 34 point is from 24.2 to 28.3 mm. The diameter of the connector at its narrowest point 36 is from 22.45 to 20.7 mm. The depth of the connector measured from its top face 38 to its opposite bottom face 40 (not including the skirt which depends from the bottom face) is from 19.75 to 22.25 mm. The angle between the wall of the connector and its axis (which is half of the angle defined by the diametrically opposite walls of the connector) is 5°. The connector is therefore a snug fit in the bore 26 in the head part, with the top face 38 located within the bore 26 in the head part, and the bottom face 40 located adjacent to the reverse face 24 of the head part. When the connector is fully received in the bore 26 in the head part, the length of the contacting surfaces of the connector and the bore, measured along the axis of the bore, is from 19.75 to 22.25 mm. The widest point at which the connector is in contact with the bore is at the widest part of the connector (that is at the bottom face 40). Accordingly, the ratio of the length of the contacting surfaces of the bore in the head part and the connector when assembled, measured along the axis of the bore in the head part, to the diameter of the bore in the head part at the widest point at which it contacts the external surface of the connector, is 1.23 (24.2:19.75) or 1.27 (28.3: 22.25) in the two embodiments which are discussed.

The connector 30 has a bore 42 within it extending from the bottom face 40. The bore is tapered inwardly in a direction away from the bottom face of the connector. The bore is open at its opposite narrow end. The bore can be blind at its narrow end. A skirt 43 surrounds the bore at its open end on the bottom face 40.

The bore 42 in the connector is sized so that the spigot 14 on the stem is a snug fit within it.

Figure 5:
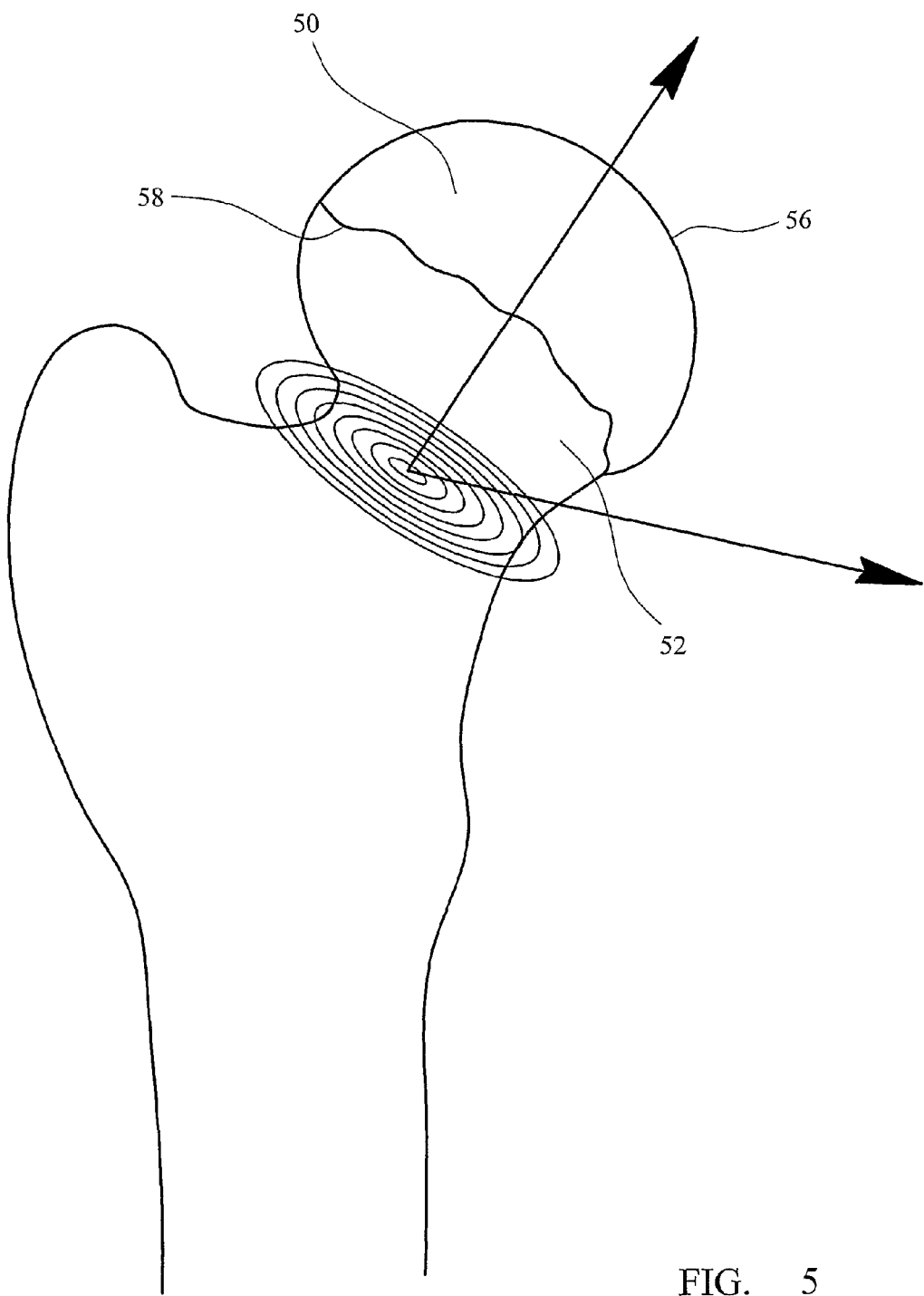
FIG. 5 is a view of the head of a femur to illustrate the offset of the bearing surface of the femoral head relative to the femoral neck.

FIG. 5 shows the head portion of a femur prior to any resection step in a procedure for replacement of a hip joint. The femur has a head part 50 and a neck 52 which extends between the head part and the femoral shaft 54. The outer bearing surface 56 of the head part is smooth, for articulation with a corresponding bearing surface within the acetabulum, and extends over the head part towards the femoral shaft to a boundary line 58. The bearing surface of the head part is defined by part of a sphere. The axis of the head part passes through the centre of the sphere, in a direction which is perpendicular to the plane which is defined by the boundary line 58.

The femoral neck 52 defines an axis which extends along its central core, between the femoral shaft and the head part.

The head part 50 of the femur can be offset relative to the femoral neck. A translational offset arises when there is a gap between the axis of the head part and the axis of the femoral neck. The size of the gap between the axes can be different from one patient to another, for example in the range 0 to 10 mm. The direction in which the axes are offset can vary, around the axis of the femoral neck.

Figure 6:
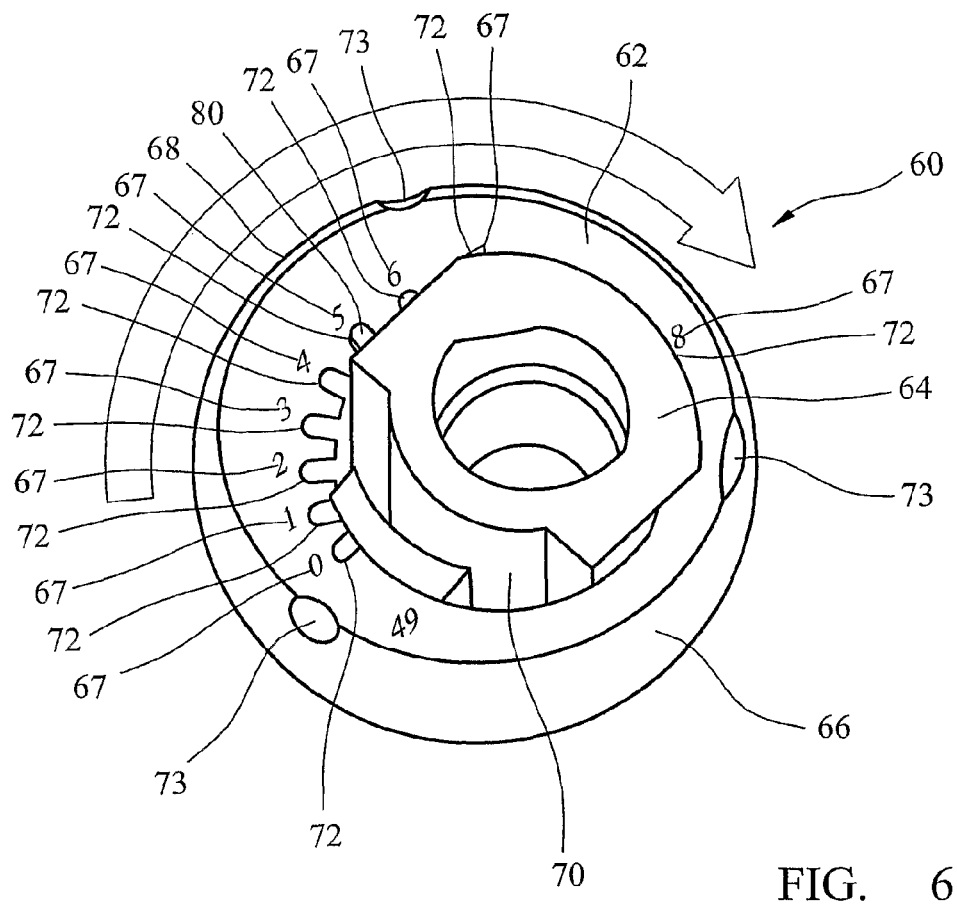
FIG. 6 is a view from below of a trial instrument which can be used to select the appropriate offset in an assembled femoral component.

FIG. 6 shows an instrument 60 which can be used to trial the head part (with its connector) on an implanted stem part. The instrument comprises a trial head 62 and a trial connector 64 (alternatively referred to herein as a connector sleeve). The trial connector 64 is shown separately in FIG. 7. The trial head has a spherical outer surface 66 which corresponds to the bearing surface of the head part of the ultimate implant, and an opposite reverse face 68. The head part has a recess 70 within it extending inwardly from the reverse face towards the bearing surface. The recess is generally round. The recess has a plurality of grooves 72 each identified by a separate marking 75 in its side wall extending parallel to the axis of the recess. The trial head can be formed from a metal such as a stainless steel or from a polymeric material.

The spherical outer surface 66 of the trial head has three notches 73 at spaced apart points. The notches are distinguishable from one another, for example by means of distinguishing markings located adjacent to the notches.

The trial connector 64 is formed from a polymeric material. It comprises a body part 74 and a trigger 76 which is connected to the body part at one end 77. The material of the trigger 76, and of the body part when the trial connector is formed as a single piece) is sufficiently resilient that the trigger can be deformed inwardly towards the body part.

The body part has a rib 80 which is dimensioned so that it can fit into one of the grooves 72 in the side wall of the recess.

The trial head and the trial connector have locking features so that the connector is retained within the recess 70 in the head part when the trigger is released, and can be removed from within the recess when the trigger is deformed towards the body part. The locking features can comprise an annular groove which extends around the recess, and a rib 81 on one or each of the body part and the trigger of the trial connector. When the rib 81 is received in the groove, the trial connector is locked against removal from the bore in the trial head. When the trigger 76 is squeezed towards the body part 74, the trial connector is able to move transversely within the recess in the body part so that the rib can be withdrawn from the groove, allowing the trial connector to be withdrawn from within the recess.

The body part 74 of the trial connector has a bore 82 formed in it. The bore is tapered inwardly in a direction away from the bottom face of the connector. The bore is open at its opposite narrow end. The bore is blind at its narrow end. The bore 82 in the trial connector is sized so that the spigot 14 on the stem is a snug fit within it.

Figure 7:
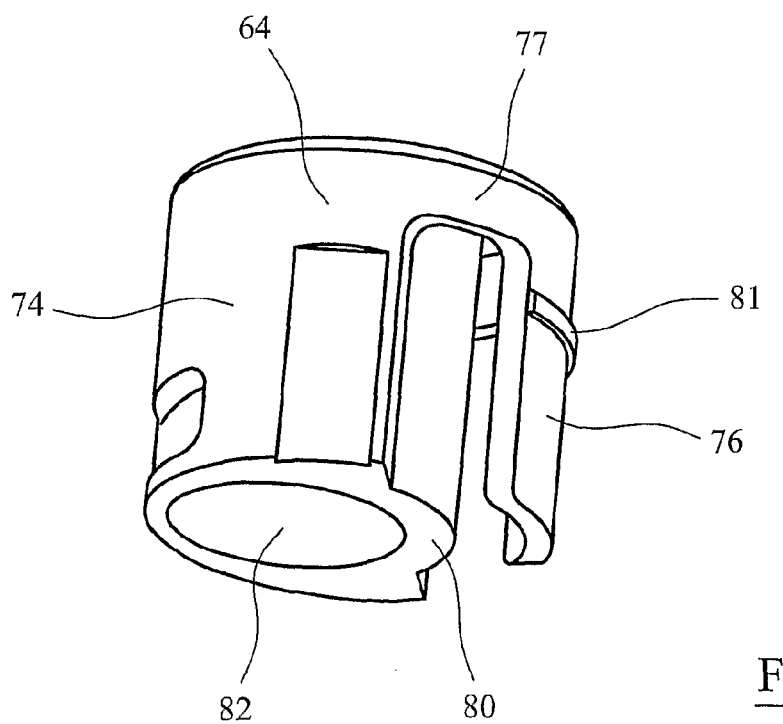
FIG. 7 is a side view of the trial connector of the trial instrument which is shown in FIG. 6.
Figure 8:
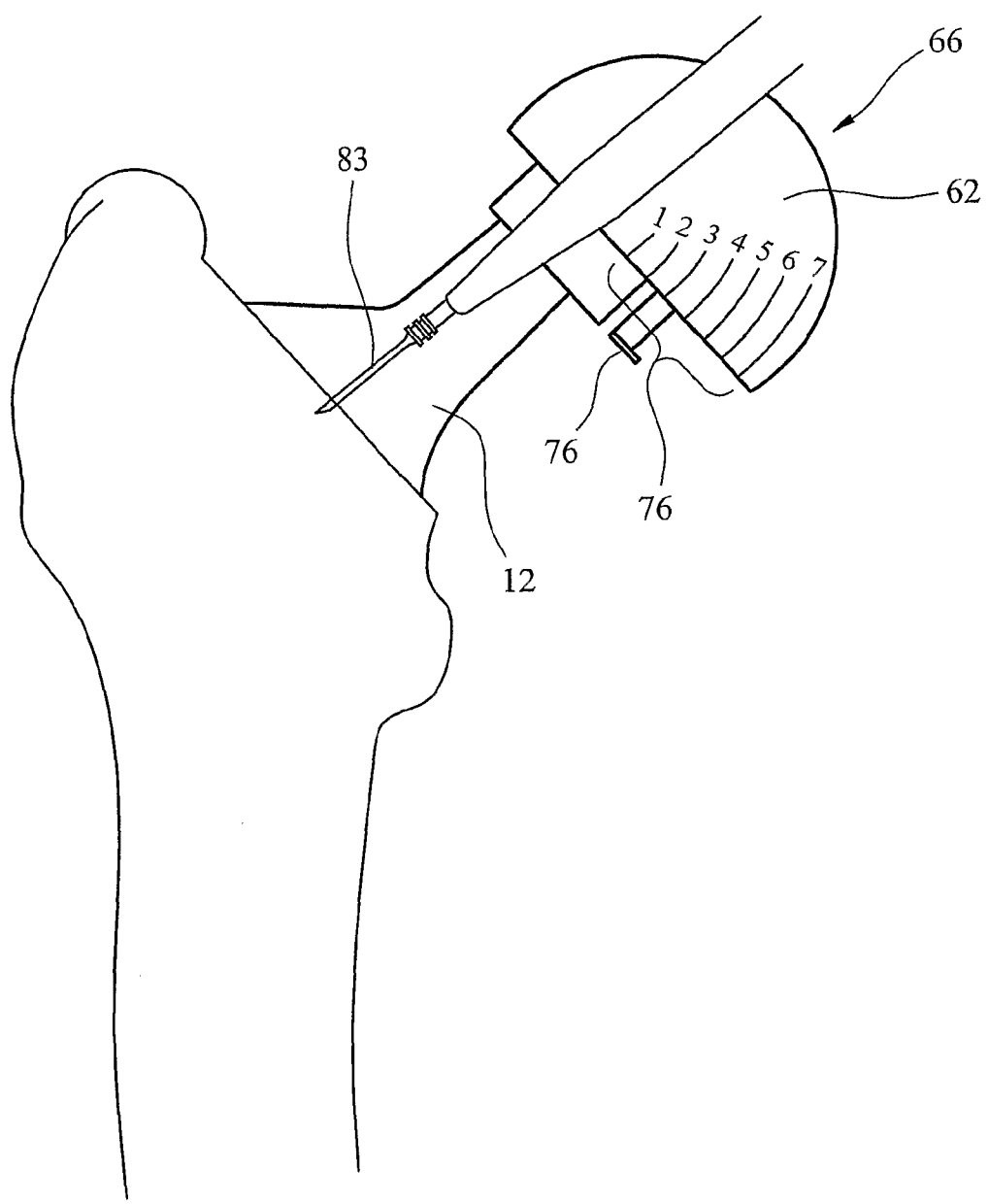
FIG. 8 is a side view of the head of the femur, with the trial instrument shown in FIG. 6 mounted on the stem part.

FIG. 8 is a side view of the head of the femur, with the trial instrument shown in FIG. 6 and FIG. 7 mounted on a stem part 12 of a femoral component of a hip joint prosthesis. FIG. 8 illustrates the trial instrument in position for trialling the offset between the axis of the trial head 62 and the axis of the stem part 12. By varying the angular position of the trial connector 64 within recess 70 the magnitude of the offset can be varied. By rotating the connector 64 about the stem part the direction of the offset can be varied.

Markings 75 on the reverse face 68 of the trial head 62 provide an indication of the size of the offset, which is then to be incorporated in the assembled head component. The markings may also be provided around the perimeter of the trial head 62. The magnitude of the offset between the axis of the trial head 62 and the axis of the bore 82 in the trial connector 64 is determined by the groove 72 within the trial head 62 engaged by the rib 80 upon the trial connector 64. Furthermore, for each groove 72, the direction of the maximum offset differs. Markings 67 about the perimeter of the trial head 62 are numbered corresponding to the markings 75 on the reverse face of the trial head 62. The corresponding marking 67 about the perimeter of the trial head for the selected groove 72 (and thus selected magnitude of offset) indicates the direction of the maximum offset. The surgeon is therefore able to appropriately determine the required magnitude of offset by engaging rib 80 into a chosen groove 72 and orientate the offset by rotating the trial instrument 60 upon stem part 12 until the marking 67 on the perimeter of the trial head 62 corresponding to the selected groove 72 points in the correct direction.

Figure 9:
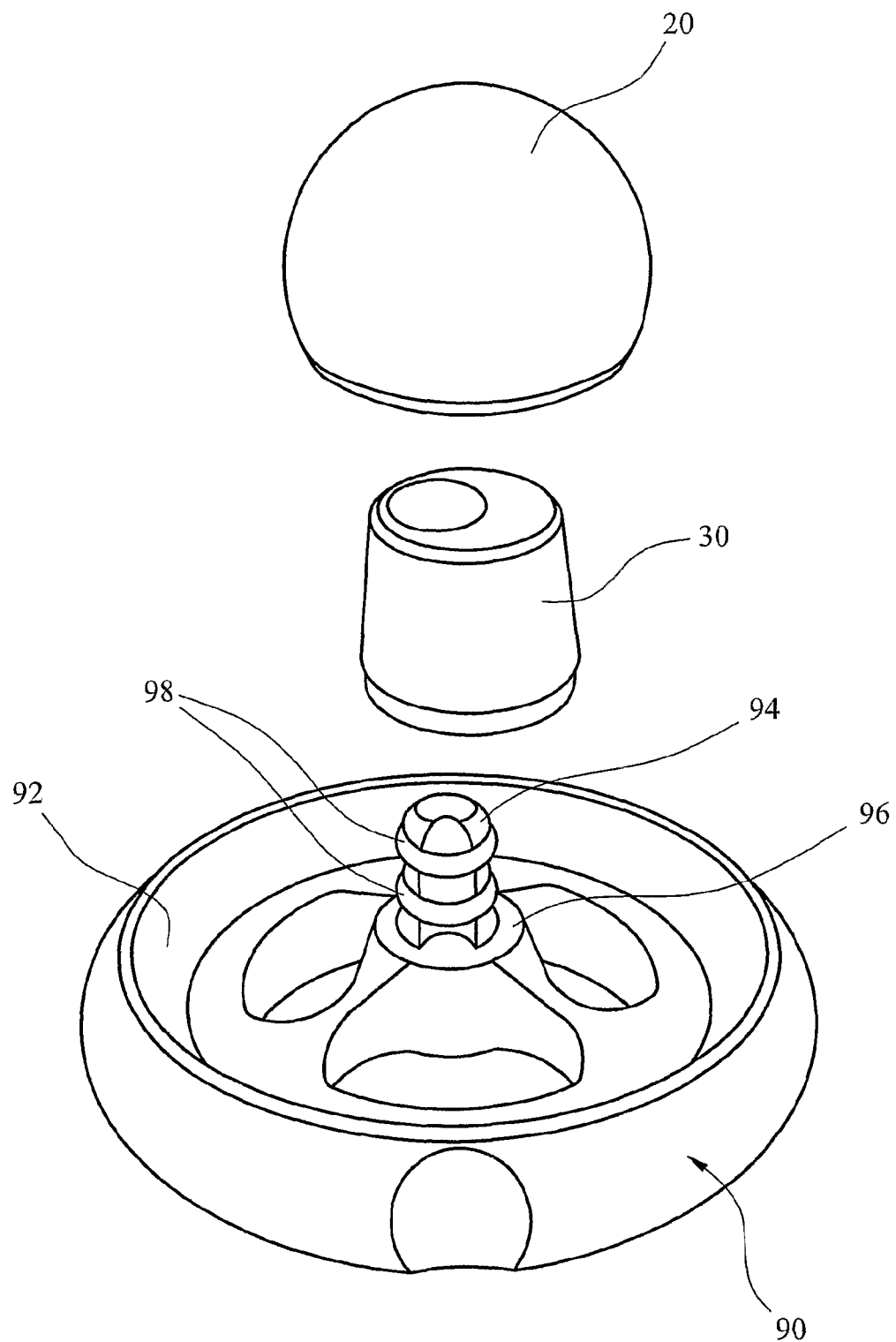
FIG. 9 is a side view of a tool which can be used to assemble the head part and the connector, shown in FIGS. 3 and 4 respectively.

FIG. 9 shows an assembly tool 90 which can be used in the assembly of the head part 20 of the femoral component and the connector 30. The tool comprises a base 92 having an upstanding spigot 94. The spigot has a collar 96 around it, which presents an upwardly facing surface. A pair of compressible O-rings 98 is provided on the spigot, located in annular grooves therein. The sizes of the spigot and the O-rings are such that the O-rings are compressed on contact with the internal wall of the bore 42 in the connector 30 when the connector is seated on the tool with the bottom face of the skirt 43 in contact with the collar 96 on the tool. This can help to retain the connector on the spigot, by virtue of the friction forces between the O-rings and the internal surface of the bore in the connector.

The assembly tool 90 is made from stainless steel. It can have a ring of a rubber material located in a groove in its lower face such that it protrudes from the groove to engage the surface on which the tool is placed when in use.

Figure 10:
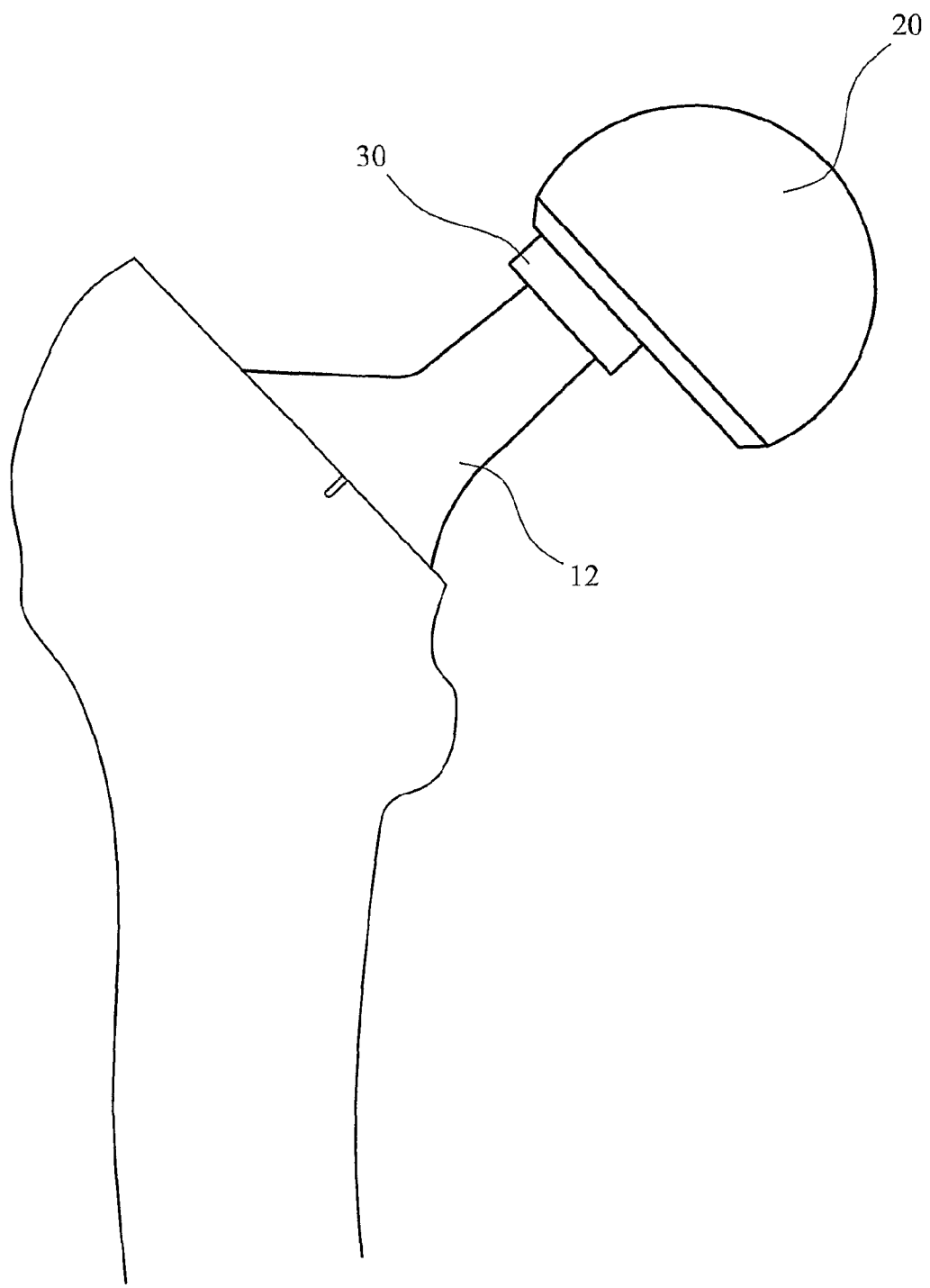
FIG. 10 is a view from one side of an assembled femoral component of a hip joint prosthesis according to the present invention.

FIG. 10 shows the femoral component of a hip joint prosthesis according to the present invention which has been assembled. The assembled femoral component comprises the head part 20, with the connector 30 located in the bore 26 therein. The spigot 14 on the stem part 12 of the femoral component is located in the bore 42 in the connector.

Dislocation and leg length discrepancy are important considerations during hip arthroplasty. The ability to offset the axis of a head part of a femoral implant from the neck axis of the femoral implant as described above has provided for an increased ability to reproduce the natural joint's biomechanics. Certain femoral stem implants have limited flexibility in terms of stem anteversion (which may be required in order to imitate the natural joint). Therefore, it can be particularly advantageous to position the head part of the femoral implant with a pronounced anterior or posterior offset.

As noted above, in connection with FIGS. 6 to 8, the orientation of the offset about the stem 12 for the trial head 62 can be determined by inspection of corresponding markings 67 about the perimeter of the trial head 62. However, for minimally invasive surgical techniques in which there is limited access to the femoral head it can be difficult to view the markings 67 about the perimeter of the trial head. The visibility of the markings 67 is especially limited when the trial implant instrument is positioned with the offset extending posteriorly or anteriorly when using anterior or posterior surgical approaches respectively as this causes the markings to be positioned such that they are directed into the wound and therefore are not visible to the surgeon.

Figure 11:
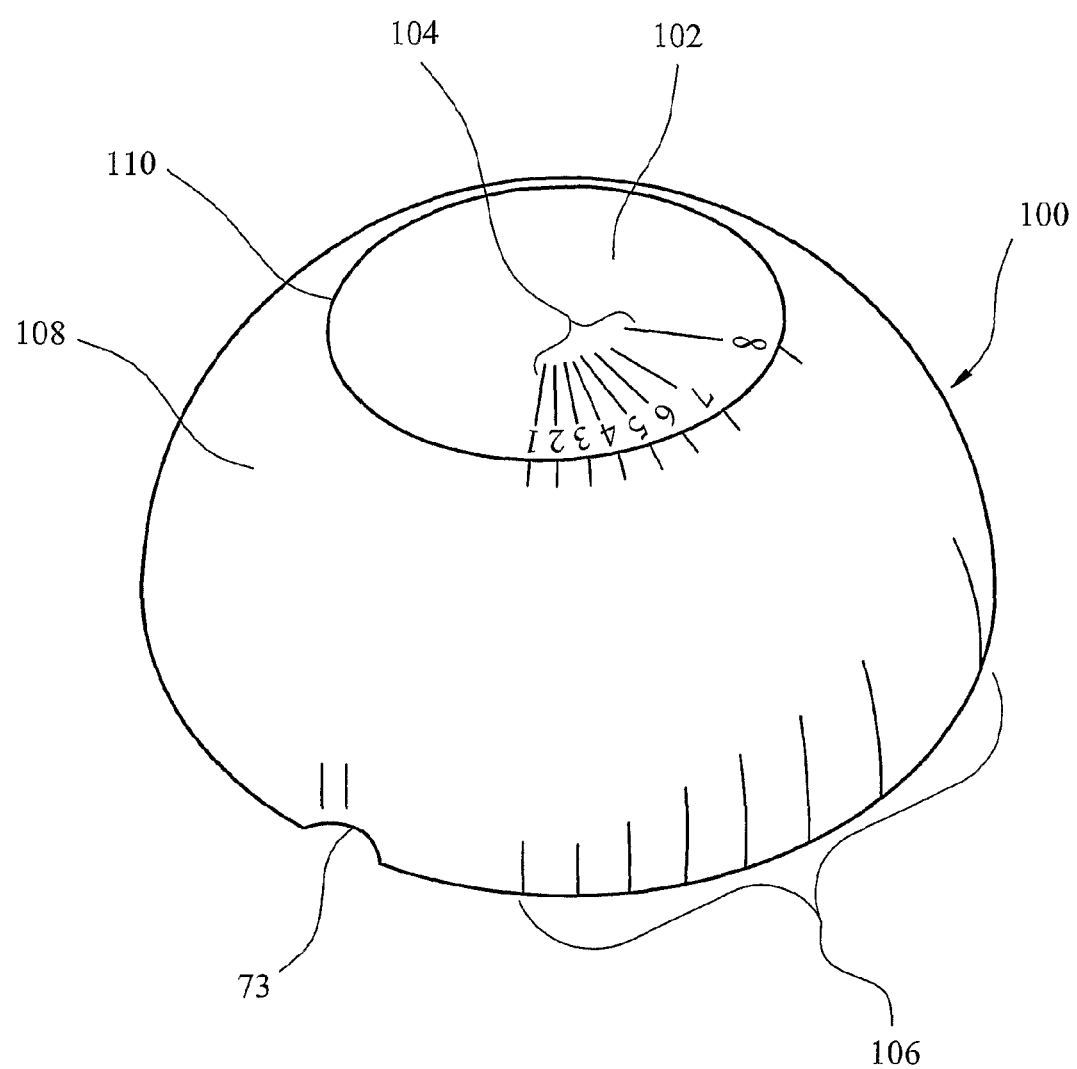
FIG. 11 is a perspective view of an alternative trial head of a trial instrument which may be substituted for the trial head shown in FIG. 6.

Referring now to FIG. 11, this illustrates an alternative trial head 100 which may be substituted for the trial head 62 illustrated in FIG. 6. In order to provide improved visibility of markings indicating the direction of offset for selected grooves 72, the pole of the trial head 100 is resected to provide a substantially flattened surface 102 to host the offset markings 104 (that is, markings that indicate the direction of the offset for a corresponding magnitude of offset which is set by setting the angular position of the trial connector within the bore in the reverse surface of trial head 100). As shown in FIG. 11, the offset markings 104 may extend from the flattened surface 102 onto the articulating surface 108. FIG. 11 further illustrates markings 106 about the perimeter of trial head 100 which are in the same position as for markings 67 for trial head 62 illustrated in FIG. 6. As can be seen, markings 104 and 106 are numbered 1 to 8 and correspond to respective grooves 72 formed in the recess 70 on the reverse surface of trial head 100 (which is the same as for trial head 62 shown in FIG. 6). Consequently, once a surgeon has selected a groove 72 to be engaged by rib 80 on the trial connector 64 (that is, the surgeon has selected the required size of offset between the axis of the trial head 100 and the axis of stem part 12) the corresponding marking 104 can be identified. The trial implant instrument 100 can then be rotated about the stem part 12 until the identified marking 104 (and also marking 106, which may not be visible to the surgeon) extends in the correct radial direction about the stem part 12.

Other than flattened surface 102 (and the markings thereon, or extending onto the articulating surface 108) trial head 100 is identical to trial head 62, and couples to trial connector 64 in the same manner. The articulating surface 108 is substantially the same as for the trial head 62 shown in FIG. 6. Three notches 73 (only one of which is visible in FIG. 11) are provided as for trial head 62, the purpose of which will be explained below.

The articulating surface 108 generally defines a portion of a sphere (as for the articulating surface of the trial head 62 shown in FIG. 6). The flattened surface 102 is located proximal to, and preferably about, the pole of the sphere (that is, the point at which the polar axis of the sphere defining the axis of the trial head exits the sphere). The sphere about the pole is resected. Preferably, the resection is performed such that the flattened surface 102 is defined by a border 110 which extends about the pole at a constant radius, although the flattened surface may not be defined by a circular border. The flattened surface may be eccentric about the polar axis. The flattened surface need not be perpendicular to the polar axis.

Advantageously, larger flattened surfaces 102 increase the visibility of the markings 104. However, larger flattened surfaces 102 reduce the extent of the articulating surface 108, and thus can interfere with the purpose of the trial implant instrument, that is checking that the final implanted prosthesis will function correctly and correctly articulate within the acetabular cup. The border 108 may be defined by the angle it subtends with the polar axis at the centre of the sphere defining the articulating surface 108. Preferably this angle is no more than 60° and no less than 20°. The flattened surface may comprise not more than 50% of surface area of the upper surface of the trial head 100. More preferably the flattened surface comprises not more than 30% and not less than 10% of the surface area of the upper surface of the trial head 100. The size of the flattened surface is limited so as to not significantly affect the articulation of the upper surface of the trial head within the acetabular cup or against the natural acetabulum. Additionally, if the resection is too deep into the trial head then it could intersect the bore in the reverse surface of the trial head. An alternative method of defining the size of the flattened surface is by reference to the reduction in the height of the trial head (measured along the polar axis of the trial head defined by the spherical articulating surface). Preferably, the height of the resected surface at the pole is no less than 70% of the height that the sphere would be if it was not resected. More preferably, the height of the resected surface at the pole is no less than 80% and no more than 95% of the height that the sphere would be if it was not resected.

It will be appreciated that flattened surface 102 need not be a true planar surface. Flattened surface 102 may be convex and defined by a radius of curvature which is at least in parts of the flattened surface greater than that of the articulating surface 108. The radius of curvature of the flattened surface need only be sufficiently increased to increase the visibility of the markings 104. Furthermore, the border 110 need not comprise a discontinuity between the flattened surface 102 and the articulating surface 108. The border 110 may be curved with a radius of curvature which increases smoothly towards the pole to provide a smooth transition between the two surfaces. Alternatively the border 110 may be chamfered.

Figure 12:
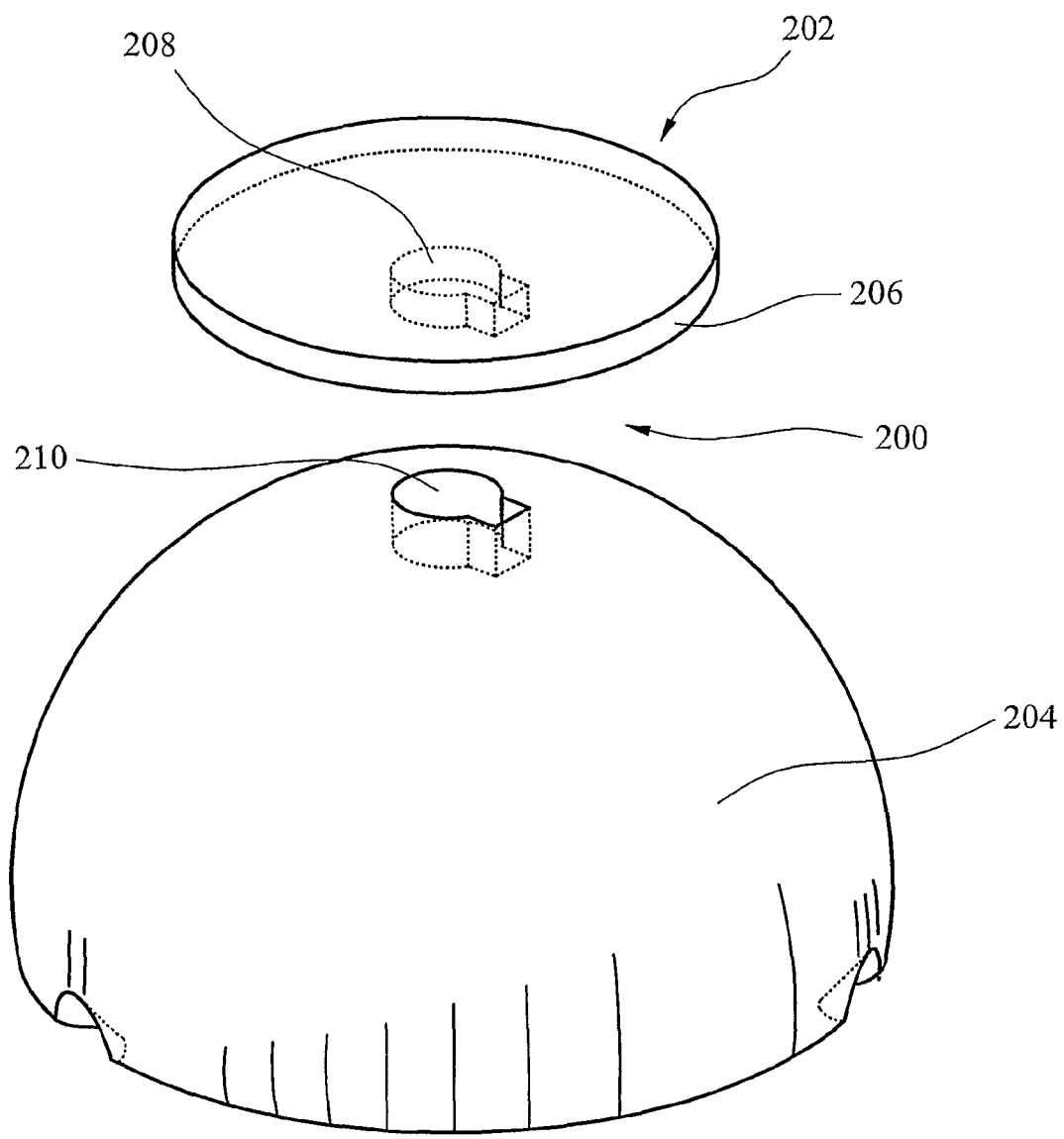
FIG. 12 is a perspective view of another alternative trial head of a trial instrument which may be substituted for the trial head shown in FIG. 6.

Referring now to FIG. 12, an alternative trial head 200 to trial head 100 is illustrated, which also provides a flattened surface 202 suitable for supporting markings, such as markings indicative of a radial direction of maximum eccentricity. However, the trial head 200 of FIG. 12 differs from trial head 100 of FIG. 11 in that the flattened surface 202 is provided as a modular component that is arranged to be detachably coupled to the spherical articulating surface 204. The spherical articulating surface 204 is therefore substantially the same as that for trial head 62 shown in FIG. 6. The modular flattened surface 202 can be coupled to the spherical articulating surface 204 when required for aligning the trial head 200 and then removed before the surgeon performs a trial joint reduction.

Advantageously, providing the flattened surface 202 as a modular component results in the trial head 200 performing substantially the same as for trial head 62 of FIG. 6 during the trial joint reduction. The modular flattened surface 202 comprises a flattened disc 206 and at least one leg 208 (shown in outline) extending towards the articulating surface 204. The leg 208 is received within a corresponding socket 210 in the articulating surface 204. Preferably the at least one socket 210 and leg 208 are arranged such that the flattened surface can only be coupled to the trial head in one rotational position. As shown in FIG. 12, the leg 208 and socket 210 are key shaped, thereby ensuring correct alignment. Alternative shapes which are not rotationally symmetrical could be used. Alternatively, three legs and sockets may be arranged such that they do not form an equilateral triangle would prevent the flattened surface being coupled to the trial head incorrectly. However, advantageously, providing only a single socket 210, such as a key shaped socket, reduces the amount of the articulating surface 204 that must be removed, reducing the impact on the articulating surface 204 during a trial reduction.

As for flattened surface 102 shown in FIG. 11, the modular flattened surface 202 may support any form of marking, not limited to markings indicating a radial direction of maximum eccentricity. Preferably the flattened surface 202 is located proximal to, or about, the pole of the spherical articulating surface 204. As for flattened surface 102, the flattened surface 202 need not be planar, or circular. Preferably, if the flattened surface 202 is curved, the radius of curvature is greater than that for the spherical articulating surface.

As an alternative to providing a flattened surface to increase the visibility of markings 106 for trial head 62, the markings 106 provided around the lower periphery of the trial head could be extended upwards to close to the pole of the trial head. It will be appreciated that this would have the effect of increasing the visibility of the markings to the surgeon, though may not be as effective at increasing their visibility as providing a flattened surface to display the markings.

A procedure in which the invention can be implemented to provide a femoral component of a hip joint prosthesis can include the following steps.

Initial steps involve preparing the femur to receive the stem part. These steps are conventional, and include resection of the neck and head of the femur, and working on the intramedullary cavity in the femoral shaft so that it is appropriately dimensioned to receive the stem part.

Preparatory work on the patient might provide information as to the desired offset of the femoral head. The trial components described above with reference to FIGS. 4 to 6 (and also FIGS. 11 and 12, and FIGS. 18 to 21 described below) can allow offsets to be assessed. Variations in the magnitude of the offset between the polar axis of the head part and the axis of the femoral stem for the final prosthesis can be trialled by changing the angular relationship between the trial head and the trial connector 64, using the trigger to release the trial connector for movement in the recess in the trial head. Variation in the radial direction of the offset around the axis of the femoral stem, can be trialled by rotating the trial components around the spigot 14 on the stem part 12. For the case in which the trial head 100 illustrated in FIG. 11 is used, the markings 104 on flattened surface 102 advantageously assist the surgeon in orientating the trial components correctly about the stem part 12 may being more visible to the surgeon than the corresponding markings 106 about the periphery of the trial head.

Markings 67 on the reverse face 68 of the trial head 62 provide an indication of the magnitude of the offset, which is then transferred to the final prosthesis components. Once the trial components are correctly orientated by reference to markings 104 (or markings 106) such that the offset extends in the correct radial direction, a record of the angular orientation of the trial head about the spigot 14 is made with reference to a selected one of the notches 73 on the spherical outer surface 66 of the trial head, using a diathermy 83 to make a mark on bone tissue 84 immediately below the selected notch as shown in FIG. 8.

The trial implant instrument 60 is then removed from the stem part 12. Trial connector 64 is intended to lock securely to the stem part 12 onto the implant femoral implant stem 12 during trialling in order to prevent the trial implant instrument 60 spinning during trialling, in particular during trial reduction of the joint to assess the configuration of the trial implant instrument. During trial reduction the trial connector 64 is further compressed on to the stem 12, which can cause it to be difficult to later remove. When removing the trial connector 64 it is important that excessive force is not applied to the femoral stem 12 as the femoral implant may not be fully set into position, and it is important not to interfere with the junction formed between the implant and the intramedullary cavity wall. In particular, it is important not to apply too great a pull-out force to the trial connector 64 along the axis of stem part 12.

Figure 13:
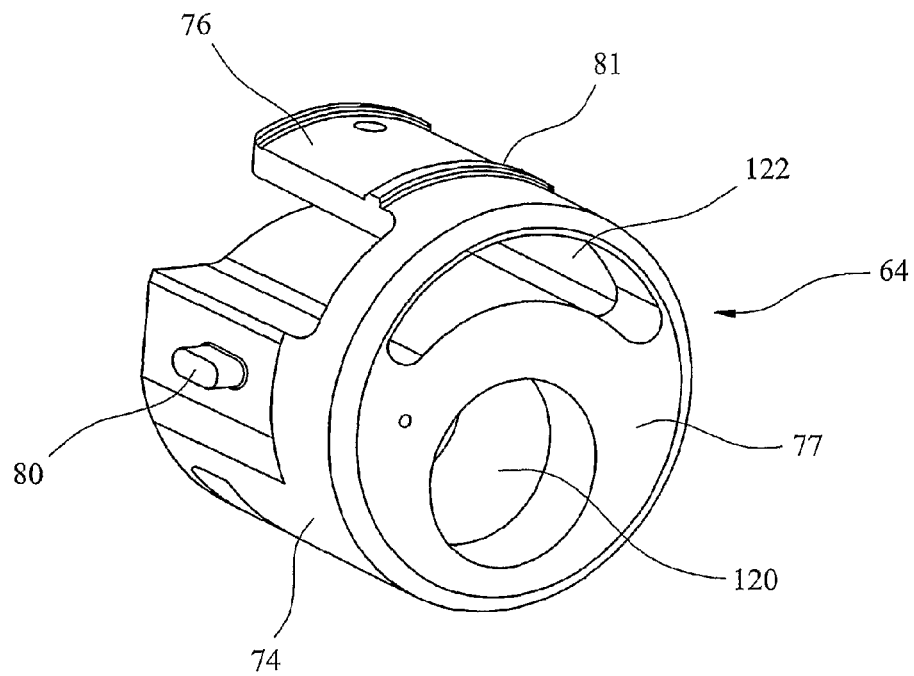
FIG. 13 is a perspective view showing a first end of the trial connector of a trial instrument as shown in FIG. 7.

FIG. 13 illustrates trial connector 64 showing the upper end 77 of the connector, (which is the face of the trial connector 64 which would be visible to a surgeon once the trial head 62, 100, 200 has been removed). Upper end 77 comprises a circular hole 120 which extends through to bore 82 which receives the stem part 12 and an curved slot 122 extending through no more than 120° of the upper surface 77 towards the outer edge of the upper surface 77 proximal the trigger 76. Curved slot 122 is not of uniform width throughout its length. Curved slot 122 is defined by an inner curved edge and an outer curved edge joined by curved ends. The inner curved edge is defined by a portion of a circle centred on the centre of the circular hole 120. The outer curved edge is defined by a portion of a circle centred on the axis of the trial connector 64. As the curvature of radius of each edge differs, the curved slot 122 is wider in the centre of the slot.

Figure 14:
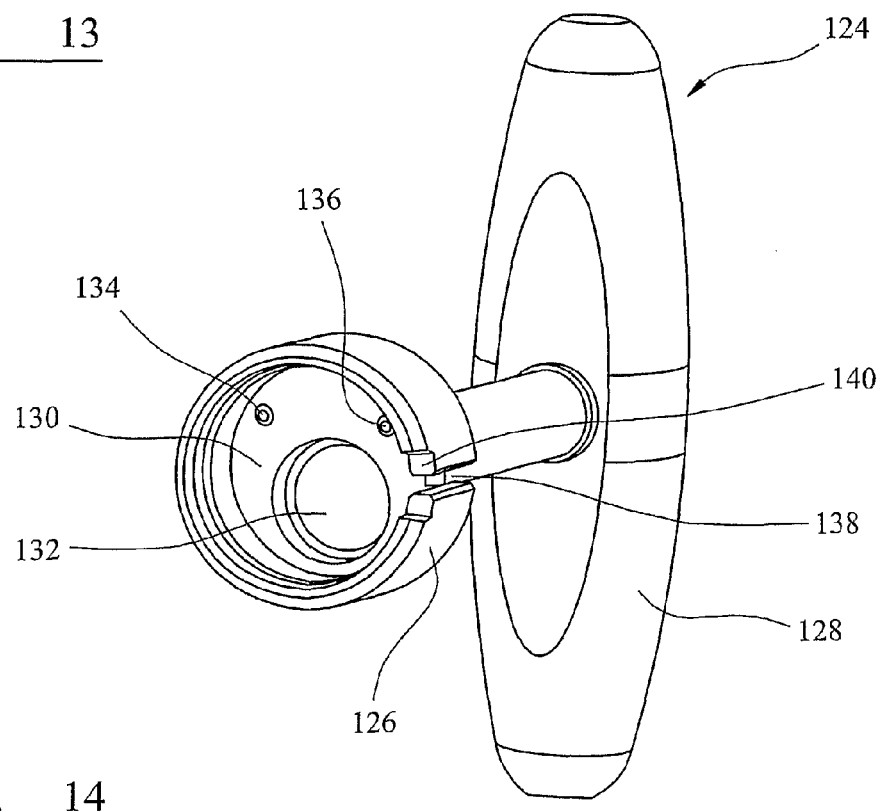
FIG. 14 is a perspective view of a trial connector removal tool suitable for removing a trial connector of a trial instrument as shown in FIG. 7 from a stem part of a femoral component of a hip joint prosthesis.

In order to assist the removal of the trial connector 64 from the implanted stem 12 a trial connector removal tool 124 is provided as illustrated in FIG. 14. The trial connector removal tool 124 comprises a generally cylindrical shell 126, which is appropriately sized to pass over trial connector 64, coupled to a handle 128. At a closed end 130 of shell 126 (coupled to handle 128) there is a circular recess 132. Circular recess 132 corresponds to hole 120 in the trial connector 64. In certain embodiments, a range of trial connectors of varying sizes may be provided. The bore within each trial connectors may differ. Specifically, the shape of the bore for each trial connector causes each trial connector to lock to the spigot at a different axial position along the spigot. For some trial connectors, the point at which the trial connector locks to the spigot may be such that the tip of the spigot extends through the hole 120 in the trial connector 64 when the trial connector 64 is tightly locked onto the femoral stem. Circular recess 132 prevents the tip of the femoral stem from limiting the insertion of the trial connector 64 into the shell 126. Extending from closed end 130 are first and second protrusions 134, 136 which are arranged to engage the curved slot 122, as will be described below. In alternative embodiments of the removal tool 124, the may be more or less protrusions for engaging the curved slot 122. For instance, there may only be a single protrusion comprising a curved rib forming the male counterpart to the female slot 122.

The shell 126 further comprises a slot 138. When the removal tool passes 124 over the trial connector 64, the slot 138 assists the surgeon in aligning the rib 80, which ensures that the protrusions 134, 136 are received in the slot 122. In order to assist the alignment of rib 80 with slot 138, the slot 138 incorporates a widened portion 140 towards the open end of shell 126. When the trial connector 64 is fully received into the removal tool 124, rib 80 extends into the widened portion 140, but does not engage the sides of the widened portion or the sides of the slot 138. Consequently, it is ensured that the rotational force is not applied to the rib 80 when the removal tool is rotated. In alternative embodiments of the invention, the rib 80 may be designed to have rotational force applied to it by the removal tool 124 in order to rotate the trial connector 64 on the spigot 14. In such embodiments the rib 80 is received in the slot and engages the sides of the slot.

In alternative embodiments of the present invention, in place of the alignment slot 138 a marking may be applied to the outside of the shell 126 for alignment with rib 80. An advantage of having slot 138 is that the surgeon will be aligning the removal tool 124 while looking along the axis of the tool. The slot 138 allows the rib 80 to remain visible through the shell 126.

Figure 15:
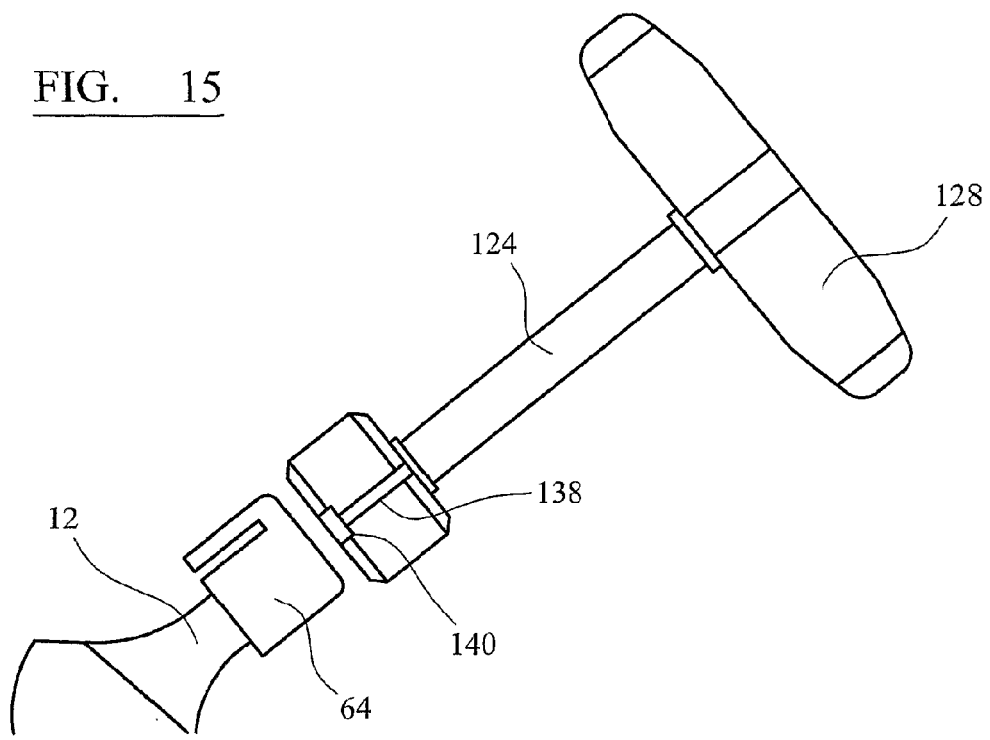
FIG. 15 illustrates the trial connector removal tool of FIG. 14 being aligned for engaging the trial connector of a trial instrument coupled to a stem part of a femoral component of a hip joint prosthesis.

Referring now to FIG. 15, this illustrates the shell of the trial connector removal tool 124 passing over the top of the trial connector 64 secured on stem part 12. Slot 138 is aligned with rib 80, thereby ensuring that the protrusions 134, 136 are correctly aligned with the curved slot 122. It alternative embodiments widened portion 140 may comprise sloping shoulders forming an outward taper at the open end of the shell to slot 138 further assisting the alignment of the rib 80 with slot 138.

Figure 16:
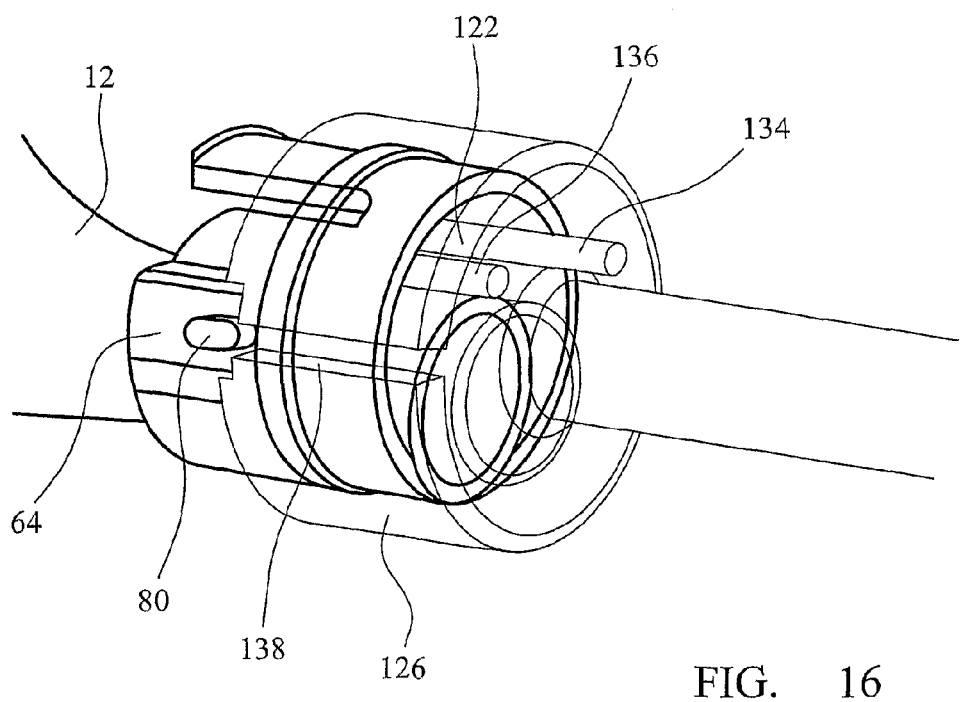
FIG. 16 illustrates the trial connector tool removal of FIG. 14 engaging a trial connector of a trial instrument coupled to a stem part of a femoral component of a hip joint prosthesis.

FIG. 16 illustrates the trial connector removal tool shell 126 fully engaged upon trial connector 64. Shell 126 is shown transparent so that the protrusions 134, 136 engaging curved slot 122 can be clearly seen. Once slot 138 is aligned with rib 80 protrusions 134, 136 are aligned with the curved slot 122. Rib 80 is not received within slot 138 when the trial connector is fully inserted into the shell 126, rather it remains in the widened portion at the open end of the slot. As shell 126 passes further over the trial connector 64 the protrusions 134, 136 are inserted into curved slot 122. In order to break the lock between the trial connector 64 and tapered spigot 14, the shell 126 can be rotated in either direction by manipulating handle 128. As the shell 126 is rotated, one or other protrusion 134, 136 engages an end of the curved slot 122 such that the rotational force is transferred to the trial connector 64. A rotational force applied to the trial connector 64 has been found to break the lock between the trial connector 64 and the spigot 14 at a much lower applied force than that required to remove the trial connector by pulling along the axis of spigot 14. Once the trial connector 64 is free to rotate upon the stem part 12 it can be easily removed by withdrawing the removal tool 124 along the axis of spigot 14. Advantageously, by reducing the amount of force required to free the trial connector 64, the risk of damaging the trial connector 64 or disturbing the femoral implant is reduced. It will be appreciated that the trial connector 64 and the trial connector removal tool 124 may be varied, so long as there remains at least one point of engagement between the two which can transfer a rotational force applied to the tool to the trial connector.

Figure 17:
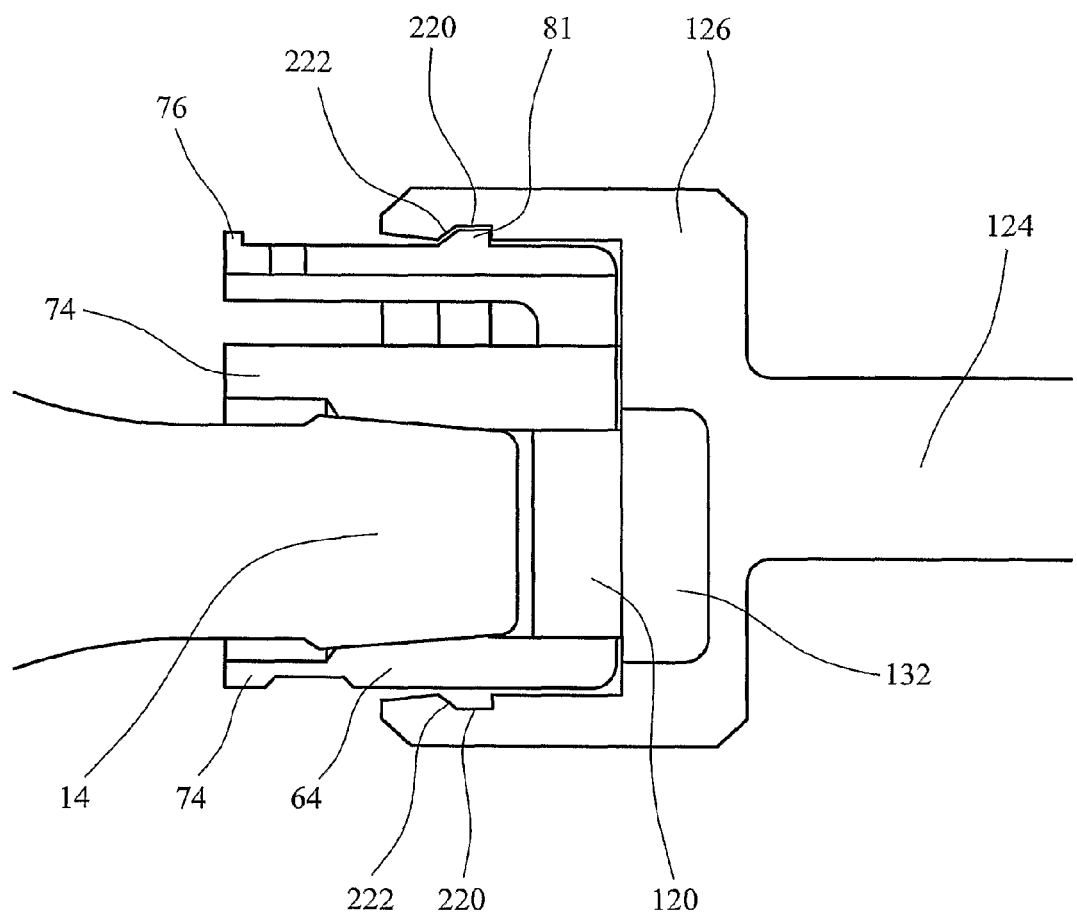
FIG. 17 is a cross sectional view of the trial connector tool of FIG. 14 engaging a trial connector of a trial instrument coupled to a stem part of a femoral component of a hip joint prosthesis.

In order to retain the trial connector 64 within the shell 126 of the removal tool 124 a partially circumferential groove 220 is provided around the inside of the shell 126. Groove 220 is arranged to receive the circumferential rib 81 provided on the trigger part 76 of the trial connector 64. FIG. 17 illustrates in cross section the connection between the trial connector 64 and the removal tool 124. When the rib 81 is received in the groove 220, the trial connector 64 is locked against removal from the shell 126. When the trigger 76 is squeezed towards the body part 74, the trial connector is able to move transversely within the shell 126 so that the rib 81 can be withdrawn from the groove 220, allowing the trial connector 64 to be withdrawn from the removal tool 124.

As discussed above, it is important not to apply excessive axial force to the trial connector 64 before the taper lock between the trial connector 64 and the spigot 14 has been broken (by applying rotational force with the removal tool 124). In order to prevent excessive axial force from being applied, the groove 220 differs from the groove within the recess 70 in the trial head. Groove 220 is provided with a sloping edge 222 on the side of the groove 220 towards the open end of the shell 126. When the trial connector 64 is inserted into the shell 126 the rib 81 snaps into groove 220 and the trial connector is retained in place. However, if the trial connector 64 is still locked to the spigot 14 and an axial force is applied to the trial connector 64 the rib 81 bears against sloping edge 222. The trigger part 76 is compress towards the body part 74 of the trial connector 64 and the rib 81 is released from groove 220. The pull out force required to release the trial connector 64 in this way from the shell 126 is much lower than the pull out force required to remove the trial connector 64 from spigot 14. Consequently, it is not possible to use removal tool 124 to remove the trial connector 64 from the spigot 13 by applying a pull out force along the axis of the spigot. Removal of the trial connector 64 from the spigot 14 using the removal tool 124 is only possible by applying a rotational force to the trial connector 64.

The size of the offset that is determined using the trial head and the trial connector is reproduced in the head component of the implant prosthesis with reference to the markings 27 on the reverse face 24 of the head part 20 (which are the counterparts to the grooves 72 in the side wall of the recess 70 in the reverse face 68 of the trial head 62), and to a marking on the connector 30 (which is the counterpart to the rib 80 on the trial connector 64). The head part 20 and the connector 40 of the implant are assembled accordingly, and placed on the spigot 94 of the assembly tool 90. An impaction force is applied to the head part through an appropriate protector (such as a block of polyethylene which is configured to be a conforming fit on the bearing surface 22 of the head part 20). Application of the impaction force causes the connector to be forced downwardly on to the spigot 94 until the skirt 43 on the bottom face of the connector contacts the collar 96 on the tool, compressing the O-rings 98 on the spigot as necessary. When the skirt on the connector contacts the collar on the tool in this way, applied impaction force leads to securing of the connection between the head part 20 and the connector 40.

The assembled head component (comprising the head part 20 and the connector 40) is positioned on the spigot 14 on the stem part 12. The rotational alignment of the head component on the stem part offset that is determined using the trial head and the trial connector is reproduced in the head component with reference to a selected one of the markings 29 on the chamfer surface 28 which is aligned with the mark on the bone made using diathermy adjacent to the corresponding notch on the trial head.

An impaction force is applied to the head component through an appropriate protector (such as a block of polyethylene which is configured to be a conforming fit on the bearing surface 22 of the head part 20) to cause the head component to become secured to the stem part. This is in line with existing assembly techniques for use with orthopaedic joint prostheses.

As discussed above, the trial heads incorporate markings to allow for identification of the direction of maximum eccentricity (that is, the offset between the axis of the femoral component neck and the axis of the head part) such that this information can be recorded and transferred to the final orthopaedic prosthesis. However, depending upon the configuration chosen for the trial implant instrument, the markings may not be easily visible to a surgeon. For instance, if a significant degree of anteversion is applied to a trial implant instrument which includes a marker indicating the radial direction of maximum eccentricity, the marker may be obscured within the wound. The problem is particularly acute for minimally invasive surgery where visibility of implants and trial implant instruments in general is limited. Limited visibility can result in misidentification of the correct marking indicating the radial direction of maximum eccentricity. That is, given that the above described trial heads incorporate multiple markings corresponding to the varying magnitudes of offset, each indicating a different direction of maximum eccentricity about the surface of the trial head relative to the stem part of the orthopaedic joint component, it is possible for confusion to arise, and the wrong marking be identified. This risk of misidentification is particularly acute if the numbers adjacent to each mark line are obscured, or if one or other end of the markings are obscured.

Figure 18:
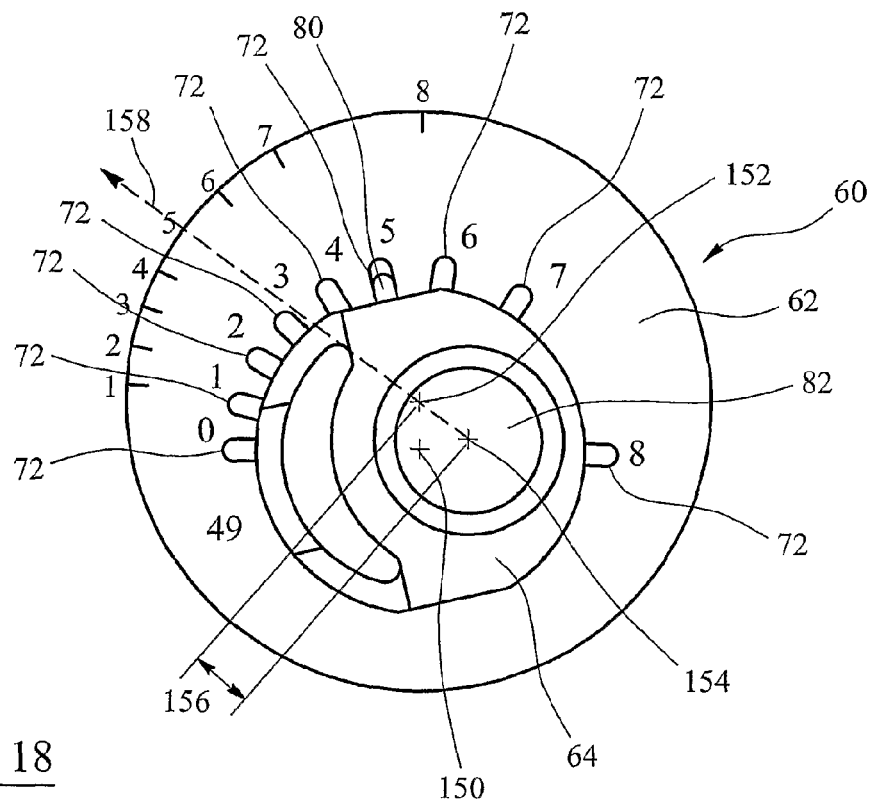
FIG. 18 is an alternative view from below of the trial instrument of FIG. 6 which can be used to select the appropriate offset in an assembled femoral component.

Referring now to FIG. 18 this illustrates the underside of the trial instrument 60 of FIG. 6, further illustrating the variation in the direction of maximum eccentricity about the centre of the stem part 12 according to the selected groove 72. As discussed above, a rib 80 forming part of trial connector 64 is engaged in a selected groove 72 within recess 70 on the underside of trial head 62. The centre 150 of the trial connector 64 is offset from the centre 152 of the trial head. The trial connector 64 is rotatable within recess 70, which is similarly offset. Trial connector 64 incorporates a recess 82, the centre 154 of which is offset from the centre 150 of the trial connector 64. Stem part 12 fits into recess 82, such that centre 154 is coincident with the axis of stem part 12.

FIG. 18 illustrates rib 80 being engaged in the groove 72 labelled "5". The magnitude of the offset between the axis of stem part 12 and the axis of the trial head is given by the distance between the centre 154 of the stem part 12 and the centre 152 of the trial head 62, and is identified by line 156. The direction of maximum eccentricity is given by a vector originating at the centre 154 of the stem part 12 and extending through the centre 152 of the trial head 62, as shown by line 158. It will be appreciated that due to the two offsets (between centres 150 and 152, and between centres 150 and 154) as the trial connector 64 is rotated within recess 70 (rib 80 being moved between grooves 72) the magnitude of the offset will vary as the angle subtended between centres 152 and 154 at centre 150 varies. Furthermore, the direction of the maximum eccentricity indicated by line 158 will vary as centre 154 (and centre 150) rotates about the centre 152 of the trial head 62.

During a surgical implantation procedure it can be difficult for the surgeon to visualise this variation in magnitude and direction of offset due to the fact that the underside of trial instrument 60 is hidden, and also due to the limited visibility of the topside of trial instrument 60 discussed above.

Figure 19:
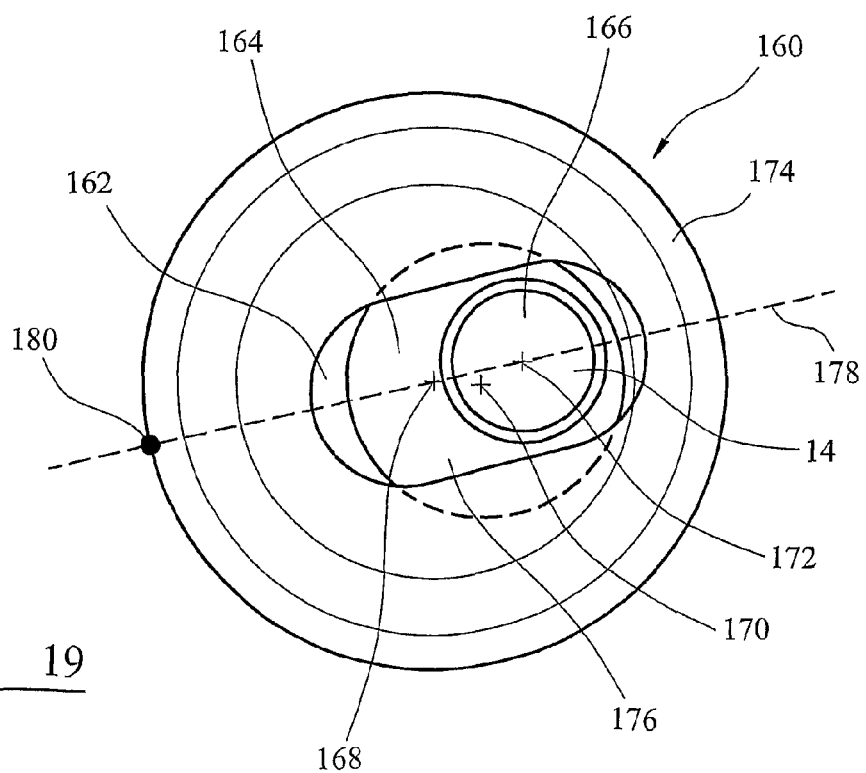
FIG. 19 is a view from below of an alternative trial instrument to that of FIGS. 6 and 18 further including a rotating indicator arranged to indicated the radial direction of maximum eccentricity.

Referring now to FIG. 19 this illustrates a modified trial instrument 160 that addresses the problem of identifying the radial direction of maximum eccentricity, and reduces the risk of misidentification due to multiple markings. FIG. 19 illustrates the underside of the trial instrument 160, including trial head 162 and trial connector 164 (although details of the coupling between the trial head 162 and the trial connector 164 have been omitted for clarity, they may be the same as illustrated in FIG. 18 for trial head 62 and trial head 64 respectively). Spigot 14 continues to be received within a recess 166 within the trial connector 164. The centre 168 of trial head 162, centre 170 of trial connector 164 and centre 172 of stem part 12 are indicated, and it can be seen that they share the same double offset arrangement as for FIG. 18.

Trial instrument 160 further includes a rotating indicator disc 174 (shown partly transparent to allow the underlying features to be seen), which substantially comprises a circular disc having the same radius as the underside of the trial head 162. Rotating indicator 174 is pivoted about the centre 168 of trial head 162 (as will be described below). Rotating indicator 174 further includes a slot 176. Stem part 12 passes through the slot 176 to engage recess 166 in trial connector 164. As the trial connector 164 is rotated within the recess in trial head 162 the stem part 12 engages the sides of slot 176 causing the rotating indicator to rotate about centre 168 of the trial head 162. During rotation of the rotating indicator 174 the spigot 14 is caused to move along the length of slot 176 as the distance between the centre 168 of the trial head 162 and the centre 172 of the stem part 12 varies.

Rotation of the rotating indicator 174 is relative to the trial head 162. The long axis 178 of slot 176 (which passes through centre 168 of trial head 162 and centre 172 of stem part 12) is aligned with the direction of maximum eccentricity of the trial head 162. Consequently, the direction of maximum eccentricity of trial head 162 about the axis of the stem part 12 for any rotational position of the trial connector 164 relative to trial head 162 can be indicated by a single mark 180 on the outside edge of the rotating indicator 174. This advantageously allows a surgeon to readily identify the direction of maximum eccentricity of the trial head 162 without having to identify which of a plurality of markings he should refer to.

Figure 20:
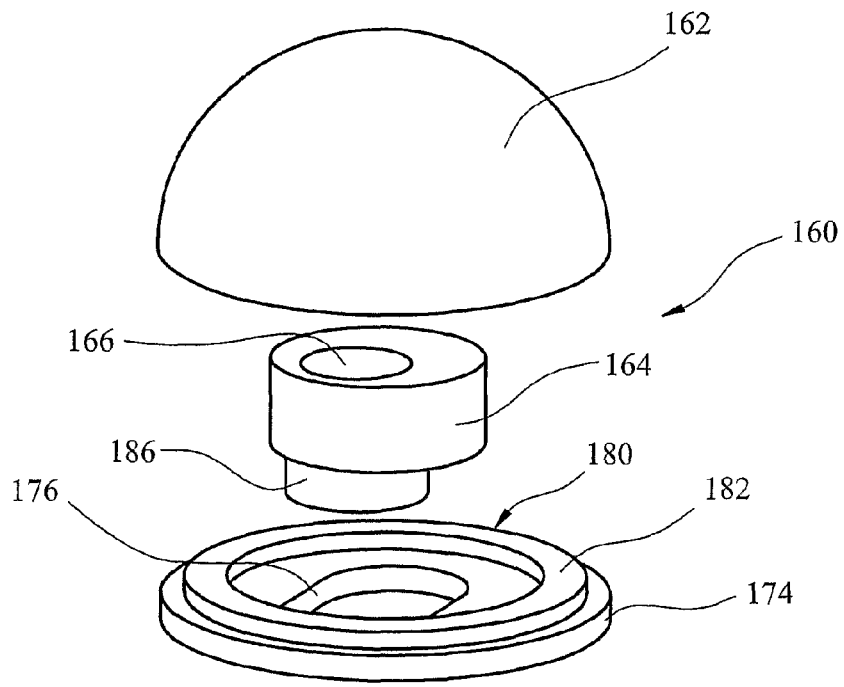
FIGS. 20 and 21 illustrate first and second partially exploded views of the alternative trial instrument of FIG. 19, illustrated partly from above and partly from below respectively.
Figure 21:
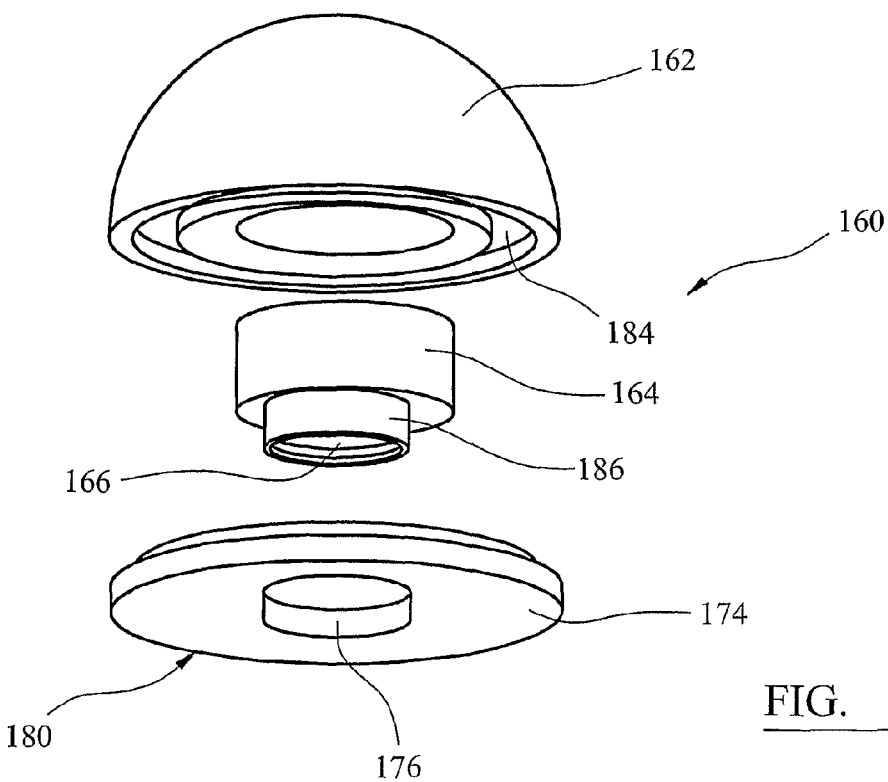

Referring now to FIGS. 20 and 21, these illustrate in exploded views trial instrument 160 in order to illustrate how the rotating indicator 174 couples to the trial head 162 and the trial connector 164. As can be seen, rotating indicator 174 substantially comprises a circular disc. On the upper surface of the rotating indicator is an annular raised portion 182. The annular raised portion 182 is received within a corresponding recess 184 on the under side of the trial head 162. The raised portion 182 and the recess 184 are both arranged to be at a constant radius about the centre 168 of the trial head 162, such that as raised portion 182 rotates within recess 184 the rotating indicator 174 pivots about the centre 168 of the trial head 162.

Trial connector 164 further incorporates a skirt portion 186 surrounding recess 166. Skirt portion 186 extends through slot 176 and has an exterior diameter matching the width of slot 176. Consequently, the exterior surface of the skirt 186 bears against the slot 176 causing the rotating indicator to rotate. It will be appreciated that stem part 12 of the orthopaedic prosthesis passes through skirt 186 such that the stem part 12 exerts pressure on the sides of the slot 176 through the skirt 186.

It will be appreciated that the shape of the rotating indicator may vary. For instance, it need not be disc shaped. The only requirements are that it rotates about the centre of the trial head and includes means whereby the stem part of the orthopaedic prosthesis can cause rotation of the rotating indicator. Typically, at least part of the rotating indicator will extend to the exterior edge of the trial head in order to display the direction of maximum eccentricity indicator. The rotating indicator may be coupled to the trial head to pivot about the centre of the trial head by direct coupling to the centre of the trial head on the underside of the trial head. Alternatively, the coupling may be achieved by the rotating indicator coupling to the trial head at least one radial position about the centre of the trial head, for instance at two diametrically opposed edges of the trial head. Furthermore, the rotating indicator need not be positioned on the underside of the trial head as shown in FIGS. 19 to 21. In alternative embodiments the rotating indicator is provided towards or at the pole of the trial head (driven by a coupling between the polar axis of the trial head and spigot 14 internal to the trial head). Providing the rotating indicator closer to the pole of the trial head advantageously increases the visibility of indicator mark 180, indicating the direction of the offset (that is, the direction of maximum eccentricity). A rotating indicator towards the pole of the trial head may take the form of a slice of the spherical articulating surface that is free to rotate relative to the remainder of the articulating surface. The slice of the articulating surface may include the pole of the trial head.

Furthermore, in alternative embodiments the connection between the trial head bore and the trial connector is smooth (that is, without the rib and groove arrangement described above in connection with FIGS. 6, 7 and 18). Consequently, the trial connector is free to rotate within the trial head bore. In such an embodiment rotating the rotating indicator relative to the trial head has the effect of driving the rotation of the trial connector within the trial head bore (thereby varying the magnitude and direction of offset). Driving the trial connector in this way has the result that the surgeon is able to set the direction of the offset by aligning the mark on the rotating indicator in the appropriate direction. The surgeon is then able to vary the magnitude of the offset by rotating the trial head while holding the rotating indicator in position. Rotating the trial head causes the trial connector to rotate within the bore in the trial head (driven by the rotating indicator) varying the magnitude of the offset.

The invention claimed is:

1. An instrument for use in a joint replacement procedure involving a bone having an intramedullary cavity, comprising:
    a trial head that corresponds to the head of an orthopaedic joint component having an upper curved surface that defines a polar axis and a lower surface, and a bore formed in the lower surface, the bore having a bore axis;
    a trial connector for connecting the trial head to a stem part of the orthopaedic joint component that is intended for location in the intramedullary cavity of the bone, wherein the trial connector can be fitted into the bore in the trial head at variable angular orientations; and
    a rotating indicator pivotally coupled about the polar axis, the rotating indicator being coupled to the trial connector such that a rotational position of the rotating indicator about the polar axis is indicative of a rotational position of the trial connector within the bore of the trial head;
    wherein the bore of the trial head is located eccentrically relative to the polar axis and the trial connector has a center and a recess located eccentrically relative to the center of the trial connector.

2. The instrument of claim 1, wherein the rotating indicator includes at least one edge arranged to engage the stem part of the orthopaedic joint component such that the rotational position of the rotating indicator about the polar axis is indicative of the rotational position of the trial connector within the bore in the trial head.

3. The instrument of claim 1, wherein the trial connector comprises a lower surface and the rotating indicator comprises a disc coupled to the lower surface of the trial connector about the polar axis.

4. The instrument of claim 3, wherein the disc is circular.

5. The instrument of claim 3, wherein the disc further comprises one of a raised annular portion and a corresponding annular recess extending about the polar axis, and the lower surface of the trial head comprises the other of one of the raised annular portion and the corresponding annular recess, the raised annular portion of one of the disc and the trial head being receivable in the recess of the other of one of the disc and the trial head to pivotally couple the rotating indicator to the lower surface of the trial head about the polar axis.

6. The instrument of claim 1, wherein the rotating indicator is pivotally coupled to the trial head.

7. The instrument of claim 6, wherein the rotating indicator further comprises at least first surface extending from near the polar axis towards the trial connector.

8. The instrument of claim 7, wherein the rotating indicator comprises a pair of parallel surfaces arranged to engage opposite sides of the stem part of the orthopaedic joint component.

9. The instrument of claim 8, wherein the pair of parallel surfaces comprises sides of a closed slot.

10. The instrument of claim 6, wherein the rotating indicator is pivotally coupled to the trial head by engagement of at least one portion of the rotating indicator that extends from the lower surface of the trial head with the upper surface of the trial head.

11. The instrument of claim 1, wherein the trial connector further comprises a skirt portion that extends from the lower surface of the trial head when the trial connector is engaged with the trial head.

12. The instrument of claim 1, wherein the rotational position of the trial connector in the trial head bore determines the rotational position of the rotating indicator.

13. The instrument of claim 1, wherein the rotational position of the rotating indicator determines the rotational position of the trial connector in the trial head bore.

14. The instrument of claim 1, wherein the trial connector recess has a recess axis, and a predetermined point on the rotating indicator is indicative of the eccentricity of the trial head relative to the recess axis.

15. An instrument for use in a joint replacement procedure involving a bone having an intramedullary cavity, comprising:
a trial head that corresponds to the head of an orthopaedic joint component having an upper curved surface that defines a polar axis and a lower surface, and a bore formed in the lower surface, the bore having a bore axis;
a trial connector for connecting the trial head to a stem part of the orthopaedic joint component that is intended for location in the intramedullary cavity of the bone, wherein the trial connector comprises a lower surface and can be fitted into the bore in the trial head at variable angular orientations;
a rotating indicator pivotally coupled about the polar axis, the rotating indicator comprises a disc coupled to the lower surface of the trial connector about the polar axis such that a rotational position of the rotating indicator about the polar axis is indicative of a rotational position of the trial connector within the bore of the trial head; and
wherein the bore of the trial head is located eccentrically relative to the polar axis and the trial connector has a center and a recess located eccentrically relative to the center of the trial connector.

16. The instrument of claim 15, wherein the disc is circular.

17. The instrument of claim 15, wherein the disc further comprises one of a raised annular portion and a corresponding annular recess extending about the polar axis, and the lower surface of the trial head comprises the other of one of the raised annular portion and the corresponding annular recess, the raised annular portion of one of the disc and the trial head being receivable in the recess of the other of one of the disc and the trial head to pivotally couple the rotating indicator to the lower surface of the trial head about the polar axis.

18. An instrument for use in a joint replacement procedure involving a bone having an intramedullary cavity, comprising:
a trial head that corresponds to the head of an orthopaedic joint component having an upper curved surface that defines a polar axis and a lower surface, and a bore formed in the lower surface, the bore having a bore axis;
a trial connector for connecting the trial head to a stem part of the orthopaedic joint component that is intended for location in the intramedullary cavity of the bone, wherein the trial connector can be fitted into the bore in the trial head at variable angular orientations; and
a rotating indicator pivotally coupled about the polar axis to the trial head, the rotating indicator being coupled to the trial connector such that a rotational position of the rotating indicator about the polar axis is indicative of a rotational position of the trial connector within the bore of the trial head;
wherein the bore of the trial head is located eccentrically relative to the polar axis and the trial connector has a center and a recess located eccentrically relative to the center of the trial connector; and wherein the rotating indicator further comprises a pair of parallel surfaces that form sides of a closed slot, the pair of surfaces being arranged to engage opposite sides of the stem part.

* * * * *